(12) United States Patent
Kim et al.

(10) Patent No.: US 8,278,058 B2
(45) Date of Patent: Oct. 2, 2012

(54) DIAGNOSTIC COMPOSITION AND KIT FOR RENAL CELL CARCINOMA

(75) Inventors: Dong Su Kim, Daegu (KR); Nam Hoon Cho, Seoul (KR); Hyung Jin Na, Pohang-si (KR); Young Deuk Choi, Seoul (KR); Jae Ho Jang, Busan (KR); Hye-Kyung Kim, Gyeongju-si (KR); Mo Yoel Park, Pohang-si (KR); Won Man Park, Pohang-si (KR); Tae-hoon Kim, Busan (KR); Dong Hee Lee, Busan (KR); Kyung Mok Park, Pohang-si (KR)

(73) Assignees: DCD Inc., Pohang-si, Gyeongsangbuk-do (KR); Genomine, Inc., Pohang-si, Gyeongsangbuk-do (KR)

( * ) Notice: Subject to any disclaimer, the term of this patent is extended or adjusted under 35 U.S.C. 154(b) by 224 days.

(21) Appl. No.: 12/672,498

(22) PCT Filed: Aug. 6, 2008

(86) PCT No.: PCT/KR2008/004562
§ 371 (c)(1), (2), (4) Date: Feb. 5, 2010

(87) PCT Pub. No.: WO2009/020343
PCT Pub. Date: Feb. 12, 2009

(65) Prior Publication Data
US 2010/0297661 A1  Nov. 25, 2010

(30) Foreign Application Priority Data

Aug. 6, 2007 (KR) .......................... 10-2007-0078436

(51) Int. Cl.
*G01N 33/53* (2006.01)
(52) U.S. Cl. ......................................................... 435/7.1
(58) Field of Classification Search ........................ None
See application file for complete search history.

(56) References Cited

U.S. PATENT DOCUMENTS 5,162,504 A   11/1992  Horoszewicz
2006/0003368 A1 *  1/2006  Tacke et al. ...................... 435/6

OTHER PUBLICATIONS

Tockman et al (Cancer Res., 1992, 52:2711s-2718s).*
WIPO, International Search Report for International Application No. PCT/KR2008/004562.

* cited by examiner

*Primary Examiner* — Sean Aeder
(74) *Attorney, Agent, or Firm* — Intellectual Property Law Group LLP

(57) ABSTRACT

Disclosed herein are a composition and a kit for diagnosing renal cell carcinoma. The composition and kit employ, as a renal cell carcinoma marker, nicotinamide N-methyltransferase, L-plastin, secretagogin, NM23A, CapG, which is an actin regulatory protein, and/or C4a anaphylatoxin.

9 Claims, 15 Drawing Sheets

SEQUENCE LISTING

```
<160> NUMBER OF SEQ ID NOS: 12

<210> SEQ ID NO 1
<211> LENGTH: 264
<212> TYPE: PRT
<213> ORGANISM: Homo sapiens

<400> SEQUENCE: 1

Met Glu Ser Gly Phe Thr Ser Lys Asp Thr Tyr Leu Ser His Phe Asn
1               5                   10                  15

Pro Arg Asp Tyr Leu Glu Lys Tyr Tyr Lys Phe Gly Ser Arg His Ser
            20                  25                  30

Ala Glu Ser Gln Ile Leu Lys His Leu Leu Lys Asn Leu Phe Lys Ile
        35                  40                  45

Phe Cys Leu Asp Gly Val Lys Gly Asp Leu Leu Ile Asp Ile Gly Ser
    50                  55                  60

Gly Pro Thr Ile Tyr Gln Leu Leu Ser Ala Cys Glu Ser Phe Lys Glu
65                  70                  75                  80

Ile Val Val Thr Asp Tyr Ser Asp Gln Asn Leu Gln Glu Leu Glu Lys
                85                  90                  95

Trp Leu Lys Lys Glu Pro Glu Ala Phe Asp Trp Ser Pro Val Val Thr
            100                 105                 110

Tyr Val Cys Asp Leu Glu Gly Asn Arg Val Lys Gly Pro Glu Lys Glu
        115                 120                 125

Glu Lys Leu Arg Gln Ala Val Lys Gln Val Leu Lys Cys Asp Val Thr
    130                 135                 140

Gln Ser Gln Pro Leu Gly Ala Val Pro Leu Pro Pro Ala Asp Cys Val
145                 150                 155                 160

Leu Ser Thr Leu Cys Leu Asp Ala Ala Cys Pro Asp Leu Pro Thr Tyr
                165                 170                 175

Cys Arg Ala Leu Arg Asn Leu Gly Ser Leu Leu Lys Pro Gly Gly Phe
            180                 185                 190

Leu Val Ile Met Asp Ala Leu Lys Ser Ser Tyr Tyr Met Ile Gly Glu
        195                 200                 205

Gln Lys Phe Ser Ser Leu Pro Leu Gly Arg Glu Ala Val Glu Ala Ala
    210                 215                 220

Val Lys Glu Ala Gly Tyr Thr Ile Glu Trp Phe Glu Val Ile Ser Gln
225                 230                 235                 240
```

Ser Tyr Ser Ser Thr Met Ala Asn Asn Glu Gly Leu Phe Ser Leu Val
            245                 250                 255

Ala Arg Lys Leu Ser Arg Pro Leu
            260

<210> SEQ ID NO 2
<211> LENGTH: 952
<212> TYPE: DNA
<213> ORGANISM: Homo sapiens

<400> SEQUENCE: 2
tgaactctgg atgctgttag cctgagactc aggaagacaa cttctgcagg gtcactccct       60
ggcttctgga ggaaagagaa ggagggcagt gctccagtgg tacagaagtg agacataatg      120
gaatcaggct tcacctccaa ggacacctat ctaagccatt ttaaccctcg ggattaccta      180
gaaaaatatt acaagtttgg ttctaggcac tctgcagaaa gccagattct taagcacctt      240
ctgaaaaatc ttttcaagat attctgccta gacggtgtga agggagacct gctgattgac      300
atcggctctg gccccactat ctatcagctc ctctctgctt gtgaatcctt taaggagatc      360
gtcgtcactg actactcaga ccagaacctg caggagctgg agaagtggct gaagaaagag      420
ccagaggcct ttgactggtc cccagtggtg acctatgtgt gtgatcttga agggaacaga      480
gtcaagggtc agagaagga ggagaagttg agacaggcgg tcaagcaggt gctgaagtgt       540
gatgtgactc agagccagcc actgggggcc gtcccttac ccccggctga ctgcgtgctc       600
agcacactgt gtctggatgc cgcctgccca gacctcccca cctactgcag ggcgctcagg      660
aacctcggca gcctactgaa gccagggggc ttcctggtga tcatggatgc gctcaagagc      720
agctactaca tgattggtga gcagaagttc tccagcctcc ccctgggccg ggaggcagta      780
gaggctgctg tgaaagaggc tggctacaca atcgaatggt ttgaggtgat ctcgcaaagt      840
tattcttcca ccatggccaa caacgaagga cttttctccc tggtggcgag gaagctgagc      900
agacccctgt gatgcctgtg acctcaatta aagcaattcc tttgacctgt ca             952

<210> SEQ ID NO 3
<211> LENGTH: 627
<212> TYPE: PRT
<213> ORGANISM: Homo sapiens

<400> SEQUENCE: 3

Met Ala Arg Gly Ser Val Ser Asp Glu Glu Met Met Glu Leu Arg Glu
1               5                   10                  15

Ala Phe Ala Lys Val Asp Thr Asp Gly Asn Gly Tyr Ile Ser Phe Asn
            20                  25                  30

Glu Leu Asn Asp Leu Phe Lys Ala Ala Cys Leu Pro Leu Pro Gly Tyr
        35                  40                  45

Arg Val Arg Glu Ile Thr Glu Asn Leu Met Ala Thr Gly Asp Leu Asp
    50                  55                  60

Gln Asp Gly Arg Ile Ser Phe Asp Glu Phe Ile Lys Ile Phe His Gly
65                  70                  75                  80

Leu Lys Ser Thr Asp Val Ala Lys Thr Phe Arg Lys Ala Ile Asn Lys
            85                  90                  95

Lys Glu Gly Ile Cys Ala Ile Gly Gly Thr Ser Glu Gln Ser Ser Val
            100                 105                 110

Gly Thr Gln His Ser Tyr Ser Glu Glu Lys Tyr Ala Phe Val Asn
        115                 120                 125

Trp Ile Asn Lys Ala Leu Glu Asn Asp Pro Asp Cys Arg His Val Ile

```
            130                 135                 140
Pro Met Asn Pro Asn Thr Asn Asp Leu Phe Asn Ala Val Gly Asp Gly
145                 150                 155                 160

Ile Val Leu Cys Lys Met Ile Asn Leu Ser Val Pro Asp Thr Ile Asp
                165                 170                 175

Glu Arg Thr Ile Asn Lys Lys Leu Thr Pro Phe Thr Ile Gln Glu
            180                 185                 190

Asn Leu Asn Leu Ala Leu Asn Ser Ala Ser Ala Ile Gly Cys His Val
                195                 200                 205

Val Asn Ile Gly Ala Glu Asp Leu Lys Glu Gly Lys Pro Tyr Leu Val
            210                 215                 220

Leu Gly Leu Leu Trp Gln Val Ile Lys Ile Gly Leu Phe Ala Asp Ile
225                 230                 235                 240

Glu Leu Ser Arg Asn Glu Ala Leu Ile Ala Leu Leu Arg Glu Gly Glu
                245                 250                 255

Ser Leu Glu Asp Leu Met Lys Leu Ser Pro Glu Glu Leu Leu Leu Arg
            260                 265                 270

Trp Ala Asn Tyr His Leu Glu Asn Ala Gly Cys Asn Lys Ile Gly Asn
                275                 280                 285

Phe Ser Thr Asp Ile Lys Asp Ser Lys Ala Tyr Tyr His Leu Leu Glu
            290                 295                 300

Gln Val Ala Pro Lys Gly Asp Glu Glu Gly Val Pro Ala Val Val Ile
305                 310                 315                 320

Asp Met Ser Gly Leu Arg Glu Lys Asp Asp Ile Gln Arg Ala Glu Cys
                325                 330                 335

Met Leu Gln Gln Ala Glu Arg Leu Gly Cys Arg Gln Phe Val Thr Ala
            340                 345                 350

Thr Asp Val Val Arg Gly Asn Pro Lys Leu Asn Leu Ala Phe Ile Ala
                355                 360                 365

Asn Leu Phe Asn Arg Tyr Pro Ala Leu His Lys Pro Glu Asn Gln Asp
            370                 375                 380

Ile Asp Trp Gly Ala Leu Glu Gly Glu Thr Arg Glu Glu Arg Thr Phe
385                 390                 395                 400

Arg Asn Trp Met Asn Ser Leu Gly Val Asn Pro Arg Val Asn His Leu
                405                 410                 415

Tyr Ser Asp Leu Ser Asp Ala Leu Val Ile Phe Gln Leu Tyr Glu Lys
            420                 425                 430

Ile Lys Val Pro Val Asp Trp Asn Arg Val Asn Lys Pro Pro Tyr Pro
                435                 440                 445

Lys Leu Gly Gly Asn Met Lys Lys Leu Glu Asn Cys Asn Tyr Ala Val
450                 455                 460

Glu Leu Gly Lys Asn Gln Ala Lys Phe Ser Leu Val Gly Ile Gly Gly
465                 470                 475                 480

Gln Asp Leu Asn Glu Gly Asn Arg Thr Leu Thr Leu Ala Leu Ile Trp
                485                 490                 495

Gln Leu Met Arg Arg Tyr Thr Leu Asn Ile Leu Glu Glu Ile Gly Gly
            500                 505                 510

Gly Gln Lys Val Asn Asp Asp Ile Ile Val Asn Trp Val Asn Glu Thr
                515                 520                 525

Leu Arg Glu Ala Glu Lys Ser Ser Ile Ser Ser Phe Lys Asp Pro
            530                 535                 540

Lys Ile Ser Thr Ser Leu Pro Val Leu Asp Leu Ile Asp Ala Ile Gln
545                 550                 555                 560
```

```
            Pro Gly Ser Ile Asn Tyr Asp Leu Leu Lys Thr Glu Asn Leu Asn Asp
                        565                 570                 575

Asp Glu Lys Leu Asn Asn Ala Lys Tyr Ala Ile Ser Met Ala Arg Lys
                    580                 585                 590

Ile Gly Ala Arg Val Tyr Ala Leu Pro Glu Asp Leu Val Glu Val Asn
                595                 600                 605

Pro Lys Met Val Met Thr Val Phe Ala Cys Leu Met Gly Lys Gly Met
                610                 615                 620

Lys Arg Val
            625

<210> SEQ ID NO 4
<211> LENGTH: 1713
<212> TYPE: DNA
<213> ORGANISM: Homo sapiens

<400> SEQUENCE: 4
atggctacag gtgatctgga ccaagatgga aggatcagct ttgatgagtt tatcaagatt        60
ttccatggcc taaaaagcac agatgttgcc aagaccttta gaaaagcaat caataagaag       120
gaagggattt gtgcaatcgg tggtacttca gagcagtcta gcgttggcac ccaacactcc       180
tattcagagg aagaaaagta tgcctttgtc aactggataa caaagccct ggaaaatgat        240 cctgattgtc ggcatgtcat cccaatgaac ccaaacacga tgatctctt taatgctgtt        300 ggagatggca ttgtcctttg taaaatgatc aacctgtcag tgccagacac aattgatgaa       360
agaacaatca caaaaagaa gctaaccct ttcaccattc aggaaaatct gaacttggct         420
ctgaactctg cctcagccat cgggtgccat gtggtcaaca tagggctga ggacctgaag        480 gaggggaagc cttatctggt cctgggactt ctgtggcaag tcatcaagat tgggttgttt       540
gctgacattg aactcagcag aaatgaagct ctgattgctc ttttgagaga aggtgagagc       600
ctggaggatt tgatgaaact ctcccctgaa gagctcttgc tgaggtgggc taattaccac       660
ctggaaaatg caggctgcaa caaaattggc aacttcagta ctgacatcaa ggactcaaaa       720
gcttattacc acctgcttga gcaggtggct ccaaaaggag atgaagaagg tgttcctgct       780
gttgttattg acatgtcagg actgcgggag aaggatgaca tccagagggc agaatgcatg       840
ctgcagcagg cggagaggct gggctgccgg cagtttgtca cagccacaga tgttgtccga       900
gggaacccca gttgaacttt ggcttttatt gccaacctct ttaacagata ccctgccctg       960
cacaaaccag agaaccagga cattgactgg ggggctcttg aaggtgagac gagagaagag      1020
cggacattta ggaactggat gaactccctg ggtgttaacc ctcgagtcaa tcatttgtac      1080
agtgacttat cagatgccct ggtcatcttc agctctatg aaaagatcaa agttcctgtt       1140
gactggaaca gagtaaacaa accgccatac cccaaactgg aggcaatat gaagaagctt       1200 gagaattgta actacgcggt agaattgggg aagaatcaag cgaagttctc cctggttggc      1260
atcggtggac aagatctcaa tgaaggaaac cgcactctca cactggcctt gatttggcag      1320
ctaatgagaa ggtatacact gaatatcctc gaagaaattg gtggtggcca gaaggtcaat      1380
gatgacatta ttgtcaactg ggtgaatgaa acattgaggg aagcagagaa aagttcatcc      1440
atctctagtt tcaaggaccc gaagattagt acaagtctgc ctgttctgga cctcatcgat      1500
gccatccaac caggttccat taactatgac cttctgaaga cagaaaatct gaatgatgat      1560
gagaaactca acaatgcaaa atatgccatc tctatggccc gaaaaattgg agcaagagtg      1620
tatgccctgc cagaagacct ggttgaagtg aaccccaaaa tggtcatgac cgtgtttgcc      1680
tgcctcatgg ggaaaggaat gaagagggtg tga                                   1713
```

<210> SEQ ID NO 5
<211> LENGTH: 276
<212> TYPE: PRT
<213> ORGANISM: Homo sapiens

<400> SEQUENCE: 5

Met Asp Ser Ser Arg Glu Pro Thr Leu Gly Arg Leu Asp Ala Ala Gly
1               5                   10                  15

Phe Trp Gln Val Trp Gln Arg Phe Asp Ala Asp Glu Lys Gly Tyr Ile
            20                  25                  30

Glu Glu Lys Glu Leu Asp Ala Phe Phe Leu His Met Leu Met Lys Leu
        35                  40                  45

Gly Thr Asp Asp Thr Val Met Lys Ala Asn Leu His Lys Val Lys Gln
    50                  55                  60

Gln Phe Met Thr Thr Gln Asp Ala Ser Lys Asp Gly Arg Ile Arg Met
65                  70                  75                  80

Lys Glu Leu Ala Gly Met Phe Leu Ser Glu Asp Glu Asn Phe Leu Leu
                85                  90                  95

Leu Phe Arg Arg Glu Asn Pro Leu Asp Ser Ser Val Glu Phe Met Gln
            100                 105                 110

Ile Trp Arg Lys Tyr Asp Ala Asp Ser Ser Gly Phe Ile Ser Ala Ala
        115                 120                 125

Glu Leu Arg Asn Phe Leu Arg Asp Leu Phe Leu His His Lys Lys Ala
    130                 135                 140

Ile Ser Glu Ala Lys Leu Glu Glu Tyr Thr Gly Thr Met Met Lys Ile
145                 150                 155                 160

Phe Asp Arg Asn Lys Asp Gly Arg Leu Asp Leu Asn Asp Leu Ala Arg
                165                 170                 175

Ile Leu Ala Leu Gln Glu Asn Phe Leu Leu Gln Phe Lys Met Asp Ala
            180                 185                 190

Cys Ser Thr Glu Glu Arg Lys Arg Asp Phe Glu Lys Ile Phe Ala Tyr
        195                 200                 205

Tyr Asp Val Ser Lys Thr Gly Ala Leu Glu Gly Pro Glu Val Asp Gly
    210                 215                 220

Phe Val Lys Asp Met Met Glu Leu Val Gln Pro Ser Ile Ser Gly Val
225                 230                 235                 240

Asp Leu Asp Lys Phe Arg Glu Ile Leu Leu Arg His Cys Asp Val Asn
                245                 250                 255

Lys Asp Gly Lys Ile Gln Lys Ser Glu Leu Ala Leu Cys Leu Gly Leu
            260                 265                 270

Lys Ile Asn Pro
        275

<210> SEQ ID NO 6
<211> LENGTH: 1437
<212> TYPE: DNA
<213> ORGANISM: Homo sapiens

<400> SEQUENCE: 6
cggcagcagc gctcgcgtcc tccccagcaa cagttactca aagctaatca gatagcgaaa      60
gaagcaggag agcaagtcaa gaaatacggt gaaggagtcc ttcccaaagt tgtctaggtc     120
cttccgcgcc ggtgcctggt cttcgtcgtc aacaccatgg acagctcccg ggaaccgact     180
ctggggcgct ggacgccgc tggcttctgg caggtctggc ggcgctttga tgcggatgaa      240
aaaggttaca tagaagagaa ggaactcgat gctttctttc tccacatgtt gatgaaactg     300

```
ggtactgatg acacggtcat gaaagcaaat ttgcacaagg tgaaacagca gtttatgact      360
acccaagatg cctctaaaga tggtcgcatt cggatgaaag agcttgctgg tatgttctta      420
tctgaggatg aaaactttct tctgctcttt cgccgggaaa acccactgga cagcagcgtg      480
gagtttatgc agatttggcg caaatatgac gctgacagca gtggctttat atcagctgct      540
gagctccgca acttcctccg agacctcttt cttcaccaca aaaaggccat ttctgaggct      600
aaactggaag aatacactgg caccatgatg aagattttg  acagaaataa agatggtcgg      660
ttggatctaa atgacttagc aaggattctg gctcttcagg aaaacttcct tctccaattt      720
aaaatggatg cttgttctac tgaagaaagg aaaagggact tgagaaaaat ctttgcctac      780
tatgatgtta gtaaaacagg agccctggaa ggcccagaag tggatgggtt tgtcaaagac      840
atgatggagc ttgtccagcc cagcatcagc ggggtggacc ttgataagtt ccgcgagatt      900
ctcctgcgtc actgcgacgt gaacaaggat ggaaaaattc agaagtctga gctggctttg      960
tgtcttgggc tgaaaatcaa cccataatcc cagactgctt tgccttttgc tcttactatg     1020
tttctgtgat cttgctggta gaattgtatc tgtgcattga tgttgggaac acagtgggca     1080
aactcacaaa tggtgtgcta ttcttgggca agaagaggga cgctagggcc ttccttccac     1140
cggcgtgatc tatccctgtc tcactgaaag cccctgtgta gtgtctgtgt tgttttccct     1200
tgaccctggg ctttcctatc ctcccaaaga ctcagctccc ctgttagatg gctctgcctg     1260
tccttcccca gtccaccagg gtggggggga caggggcagc tgagtgcatt cattttgtgc     1320
ttttgttgtg ggctttctgc ttagtctgaa aggtgtgtgg cattcatggc aatcctgtaa     1380
cttcaacata gattttttt  gtgtgtgtgg aaataaatct gcaattggaa acaaccg        1437
```

<210> SEQ ID NO 7
<211> LENGTH: 177
<212> TYPE: PRT
<213> ORGANISM: Homo sapiens

<400> SEQUENCE: 7

```
Met Val Leu Leu Ser Thr Leu Gly Ile Val Phe Gln Gly Glu Gly Pro
1               5                   10                  15

Pro Ile Ser Ser Cys Asp Thr Gly Thr Met Ala Asn Cys Glu Arg Thr
            20                  25                  30

Phe Ile Ala Ile Lys Pro Asp Gly Val Gln Arg Gly Leu Val Gly Glu
        35                  40                  45

Ile Ile Lys Arg Phe Glu Gln Lys Gly Phe Arg Leu Val Gly Leu Lys
    50                  55                  60

Phe Met Gln Ala Ser Glu Asp Leu Leu Lys Glu His Tyr Val Asp Leu
65                  70                  75                  80

Lys Asp Arg Pro Phe Phe Ala Gly Leu Val Lys Tyr Met His Ser Gly
                85                  90                  95

Pro Val Val Ala Met Val Trp Glu Gly Leu Asn Val Val Lys Thr Gly
            100                 105                 110

Arg Val Met Leu Gly Glu Thr Asn Pro Ala Asp Ser Lys Pro Gly Thr
        115                 120                 125

Ile Arg Gly Asp Phe Cys Ile Gln Val Gly Arg Asn Ile Ile His Gly
    130                 135                 140

Ser Asp Ser Val Glu Ser Ala Glu Lys Glu Ile Gly Leu Trp Phe His
145                 150                 155                 160

Pro Glu Glu Leu Val Asp Tyr Thr Ser Cys Ala Gln Asn Trp Ile Tyr
                165                 170                 175
```

Glu

<210> SEQ ID NO 8
<211> LENGTH: 1031
<212> TYPE: DNA
<213> ORGANISM: Homo sapiens

<400> SEQUENCE: 8

```
gcagaagcgt tccgtgcgtg caagtgctgc gaaccacgtg ggtcccgggc gcgtttcggg        60
tgctggcggc tgcagccgga gttcaaacct aagcagctgg aagggccctg tggctaggta       120
ccatagagtc tctacacagg actaagtcag cctggtgtgc aggggaggca gacacacaaa       180
cagaaaattg gactacagtg ctaagatgct gtaagaagag gttaactaaa ggacaggaag       240
atggggccaa gagatggtgc tactgtctac tttagggatc gtctttcaag gcaggggcc        300
tcctatctca agctgtgata caggaaccat ggccaactgt gagcgtacct tcattgcgat       360
caaaccagat ggggtccagc ggggtcttgt gggagagatt atcaagcgtt ttgagcagaa       420
aggattccgc cttgttggtc tgaaattcat gcaagcttcc gaagatcttc tcaaggaaca       480
ctacgttgac ctgaaggacc gtccattctt gccggcctg gtgaaataca tgcactcagg       540
gccggtagtt gccatggtct gggaggggct gaatgtggtg aagacgggcc gagtcatgct       600
cggggagacc aaccctgcag actccaagcc tgggaccatc cgtggagact ctgcataca       660
agttggcagg aacattatac atggcagtga ttctgtggag agtgcagaga aggagatcgg       720
cttgtggttt caccctgagg aactggtaga ttacacgagc tgtgctcaga actggatcta       780
tgaatgacag gagggcagac cacattgctt ttcacatcca tttccctcc ttcccatggg        840
cagaggacca ggctgtagga aatctagtta tttacaggaa cttcatcata atttggaggg       900
aagctcttgg agctgtgagt tctccctgta cagtgttacc atccccgacc atctgattaa       960
aatgcttcct cccagcatag gattcattga gttggttact tcatattgtt gcattgcttt      1020
tttttccttc t                                                           1031
```

<210> SEQ ID NO 9
<211> LENGTH: 348
<212> TYPE: PRT
<213> ORGANISM: Homo sapiens

<400> SEQUENCE: 9

```
Met Tyr Thr Ala Ile Pro Gln Ser Gly Ser Phe Pro Gly Ser Val
1               5                   10                  15

Gln Asp Pro Gly Leu His Val Trp Arg Val Glu Lys Leu Lys Pro Val
            20                  25                  30

Pro Val Ala Gln Glu Asn Gln Gly Val Phe Phe Ser Gly Asp Ser Tyr
        35                  40                  45

Leu Val Leu His Asn Gly Pro Glu Glu Val Ser His Leu His Leu Trp
    50                  55                  60

Ile Gly Gln Gln Ser Ser Arg Asp Glu Gln Gly Ala Cys Ala Val Leu
65                  70                  75                  80

Ala Val His Leu Asn Thr Leu Leu Gly Glu Arg Pro Val Gln His Arg
                85                  90                  95

Glu Val Gln Gly Asn Glu Ser Asp Leu Phe Met Ser Tyr Phe Pro Arg
            100                 105                 110

Gly Leu Lys Tyr Gln Glu Gly Gly Val Glu Ser Ala Phe His Lys Thr
        115                 120                 125

Ser Thr Gly Ala Pro Ala Ala Ile Lys Lys Leu Tyr Gln Val Lys Gly
    130                 135                 140
```

```
Lys Lys Asn Ile Arg Ala Thr Glu Arg Ala Leu Asn Trp Asp Ser Phe
145                 150                 155                 160

Asn Thr Gly Asp Cys Phe Ile Leu Asp Leu Gly Gln Asn Ile Phe Ala
            165                 170                 175

Trp Cys Gly Gly Lys Ser Asn Ile Leu Glu Arg Asn Lys Ala Arg Asp
            180                 185                 190

Leu Ala Leu Ala Ile Arg Asp Ser Glu Arg Gln Gly Lys Ala Gln Val
        195                 200                 205

Glu Ile Val Thr Asp Gly Glu Pro Ala Glu Met Ile Gln Val Leu
    210                 215                 220

Gly Pro Lys Pro Ala Leu Lys Glu Gly Asn Pro Glu Glu Asp Leu Thr
225                 230                 235                 240

Ala Asp Lys Ala Asn Ala Gln Ala Ala Leu Tyr Lys Val Ser Asp
            245                 250                 255

Ala Thr Gly Gln Met Asn Leu Thr Lys Val Ala Asp Ser Ser Pro Phe
            260                 265                 270

Ala Leu Glu Leu Leu Ile Ser Asp Asp Cys Phe Val Leu Asp Asn Gly
        275                 280                 285

Leu Cys Gly Lys Ile Tyr Ile Trp Lys Gly Arg Lys Ala Asn Glu Lys
    290                 295                 300

Glu Arg Gln Ala Ala Leu Gln Val Ala Glu Gly Phe Ile Ser Arg Met
305                 310                 315                 320

Gln Tyr Ala Pro Asn Thr Gln Val Glu Ile Leu Pro Gln Gly Arg Glu
            325                 330                 335

Ser Pro Ile Phe Lys Gln Phe Phe Lys Asp Trp Lys
            340                 345
```

<210> SEQ ID NO 10
<211> LENGTH: 944
<212> TYPE: DNA
<213> ORGANISM: Homo sapiens

<400> SEQUENCE: 10

```
atctgaagac agcatgtaca cagccattcc ccagaggtaa gctgcatgcc ccatctcctt      60
tcacaacttc cccttcttta cctccaagcg ctgcccctcc ccactgctct ccgcctgccc     120
agggctgtgc ttgggcaagt gggtccaggc tgctgtcaac cctctctctt ctcgcagtgg     180
ctctccattc ccaggctcag tgcaggatcc aggcctgcat gtgtggcggg tggagaagct     240
gaagccggtg cctgtggcgc aagagaacca gggcgtcttc ttctcggggg actcctacct     300
agtgctgcac aatggcccag aagaggtttc ccatctgcac ctgtggatag gtaaggggat     360
ctggatgggg gaaggttggg cccaggaagg ggagggaggg ggctggtatg gatcacaagc     420
cttgccctgc cctctcccac ttgtcccagg ccagcagtca tcccgggatg agcaggggc      480
ctgtgccgtg ctggctgtgc acctcaacac gctgctggga gagcggcctg tgcagcaccg     540
cgaggtgcag ggcaatgagt ctgacctctt catgagctac ttcccacggg gcctcaagta     600
ccaggtcaga gccacctct aggcaccccc accctgcttc tggctggttc tcaccctgca     660
gaagacccgg gtgcctttgg agccgggtcc ccacctttct gcccgtcttc cagtgggatg     720
gggtgcagag ggctctgggt ctcctgtcag tccactcaga tgggccgtct gggctgcagg     780
aaggtggtgt ggagtcagca tttcacaaga cctccacagg agcccagct gccatcaaga     840
aactctacca ggtgaagggg aagaagaaca tccgtgccac cgagcgggca ctgaactggg     900
acagcttcaa cactggggac tgcttcatcc tggacctggg ccag                     944
```

```
<210> SEQ ID NO 11
<211> LENGTH: 1744
<212> TYPE: PRT
<213> ORGANISM: Homo sapiens

<400> SEQUENCE: 11

Met Arg Leu Leu Trp Gly Leu Ile Trp Ala Ser Ser Phe Phe Thr Leu
 1               5                  10                  15

Ser Leu Gln Lys Pro Arg Leu Leu Phe Ser Pro Ser Val Val His
             20                  25                  30

Leu Gly Val Pro Leu Ser Val Gly Val Gln Leu Gln Asp Val Pro Arg
         35                  40                  45

Gly Gln Val Val Lys Gly Ser Val Phe Leu Arg Asn Pro Ser Arg Asn
     50                  55                  60

Asn Val Pro Cys Ser Pro Lys Val Asp Phe Thr Leu Ser Ser Glu Arg
 65                  70                  75                  80

Asp Phe Ala Leu Leu Ser Leu Gln Val Pro Leu Lys Asp Ala Lys Ser
                 85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
    290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
        355                 360                 365

Leu Asp Leu Ser Lys Thr Lys Arg His Leu Val Pro Gly Ala Pro Phe
    370                 375                 380
```

```
Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
            420                 425                 430

Ile Pro Ile Ile Ile Pro Gln Thr Ile Ser Glu Leu Gln Leu Ser Val
            435                 440                 445

Ser Ala Gly Ser Pro His Pro Ala Ile Ala Arg Leu Thr Val Ala Ala
            450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
                500                 505                 510

Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
                565                 570                 575

Gly Ala Lys Gln Tyr Arg Asn Gly Glu Ser Val Lys Leu His Leu Glu
                580                 585                 590

Thr Asp Ser Leu Ala Leu Val Ala Leu Gly Ala Leu Asp Thr Ala Leu
            595                 600                 605

Tyr Ala Ala Gly Ser Lys Ser His Lys Pro Leu Asn Met Gly Lys Val
610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
                645                 650                 655

Gly Asp Gln Trp Thr Leu Ser Arg Lys Arg Leu Ser Cys Pro Lys Glu
                660                 665                 670

Lys Thr Thr Arg Lys Lys Arg Asn Val Asn Phe Gln Lys Ala Ile Asn
                675                 680                 685

Glu Lys Leu Gly Gln Tyr Ala Ser Pro Thr Ala Lys Arg Cys Cys Gln
            690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
                725                 730                 735

Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Asp Leu Ile Asp
            755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
                805                 810                 815
```

```
Lys Gly Leu Cys Val Ala Thr Pro Val Gln Leu Arg Val Phe Arg Glu
            820                 825                 830

Phe His Leu His Leu Arg Leu Pro Met Ser Val Arg Arg Phe Glu Gln
            835                 840                 845

Leu Glu Leu Arg Pro Val Leu Tyr Asn Tyr Leu Asp Lys Asn Leu Thr
        850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                885                 890                 895

Val Ala Phe Ser Val Val Pro Thr Ala Ala Ala Val Ser Leu Lys
            900                 905                 910

Val Val Ala Arg Gly Ser Phe Glu Phe Pro Val Gly Asp Ala Val Ser
            915                 920                 925

Lys Val Leu Gln Ile Glu Lys Glu Gly Ala Ile His Arg Glu Glu Leu
        930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
            980                 985                 990

Gly Ala Leu Ser Pro Gly Gly Val  Ala Ser Leu Leu Arg Leu Pro Arg
            995                 1000                1005

Gly Cys  Gly Glu Gln Thr  Met Ile Tyr Leu Ala Pro  Thr Leu Ala
    1010                 1015                1020

Ala Ser  Arg Tyr Leu Asp  Lys Thr Glu Gln Trp Ser  Thr Leu Pro
    1025                 1030                1035

Pro Glu  Thr Lys Asp His  Ala Val Asp Leu Ile Gln  Lys Gly Tyr
    1040                 1045                1050

Met Arg  Ile Gln Gln Phe  Arg Lys Ala Asp Gly Ser  Tyr Ala Ala
    1055                 1060                1065

Trp Leu Ser Arg Asp Ser Ser  Thr Trp Leu Thr Ala  Phe Val Leu
    1070                 1075                1080

Lys Val  Leu Ser Leu Ala Gln  Glu Gln Val Gly Gly  Ser Pro Glu
    1085                 1090                1095

Lys Leu  Gln Glu Thr Ser Asn  Trp Leu Leu Ser Gln  Gln Gln Ala
    1100                 1105                1110

Asp Gly  Ser Phe Gln Asp  Pro Cys Pro Val Leu Asp  Arg Ser Met
    1115                 1120                1125

Gln Gly  Gly Leu Val Gly Asn  Asp Glu Thr Val Ala  Leu Thr Ala
    1130                 1135                1140

Phe Val  Thr Ile Ala Leu His  His Gly Leu Ala Val  Phe Gln Asp
    1145                 1150                1155

Glu Gly  Ala Glu Pro Leu Lys  Gln Arg Val Glu Ala  Ser Ile Ser
    1160                 1165                1170

Lys Ala  Asn Ser Phe Leu Gly  Glu Lys Ala Ser Ala  Gly Leu Leu
    1175                 1180                1185

Gly Ala  His Ala Ala Ala Ile  Thr Ala Tyr Ala Leu  Ser Leu Thr
    1190                 1195                1200

Lys Ala  Pro Val Asp Leu Leu  Gly Val Ala His Asn  Asn Leu Met
    1205                 1210                1215

Ala Met  Ala Gln Glu Thr Gly  Asp Asn Leu Tyr Trp  Gly Ser Val
```

```
                      1220            1225            1230

Thr Gly Ser Gln Ser Asn Ala Val Ser Pro Thr Pro Ala Pro Arg
            1235            1240            1245

Asn Pro Ser Asp Pro Met Pro Gln Ala Pro Ala Leu Trp Ile Glu
            1250            1255            1260

Thr Thr Ala Tyr Ala Leu Leu His Leu Leu Leu His Glu Gly Lys
            1265            1270            1275

Ala Glu Met Ala Asp Gln Ala Ser Ala Trp Leu Thr Arg Gln Gly
            1280            1285            1290

Ser Phe Gln Gly Gly Phe Arg Ser Thr Gln Asp Thr Val Ile Ala
            1295            1300            1305

Leu Asp Ala Leu Ser Ala Tyr Trp Ile Ala Ser His Thr Thr Glu
            1310            1315            1320

Glu Arg Gly Leu Asn Val Thr Leu Ser Ser Thr Gly Arg Asn Gly
            1325            1330            1335

Phe Lys Ser His Ala Leu Gln Leu Asn Asn Arg Gln Ile Arg Gly
            1340            1345            1350

Leu Glu Glu Glu Leu Gln Phe Ser Leu Gly Ser Lys Ile Asn Val
            1355            1360            1365

Lys Val Gly Gly Asn Ser Lys Gly Thr Leu Lys Val Leu Arg Thr
            1370            1375            1380

Tyr Asn Val Leu Asp Met Lys Asn Thr Thr Cys Gln Asp Leu Gln
            1385            1390            1395

Ile Glu Val Thr Val Lys Gly His Val Glu Tyr Thr Met Glu Ala
            1400            1405            1410

Asn Glu Asp Tyr Glu Asp Tyr Glu Tyr Asp Glu Leu Pro Ala Lys
            1415            1420            1425

Asp Asp Pro Asp Ala Pro Leu Gln Pro Val Thr Pro Leu Gln Leu
            1430            1435            1440

Phe Glu Gly Arg Arg Asn Arg Arg Arg Glu Ala Pro Lys Val
            1445            1450            1455

Val Glu Glu Gln Glu Ser Arg Val His Tyr Thr Val Cys Ile Trp
            1460            1465            1470

Arg Asn Gly Lys Val Gly Leu Ser Gly Met Ala Ile Ala Asp Val
            1475            1480            1485

Thr Leu Leu Ser Gly Phe His Ala Leu Arg Ala Asp Leu Glu Lys
            1490            1495            1500

Leu Thr Ser Leu Ser Asp Arg Tyr Val Ser His Phe Glu Thr Glu
            1505            1510            1515

Gly Pro His Val Leu Leu Tyr Phe Asp Ser Val Pro Thr Ser Arg
            1520            1525            1530

Glu Cys Val Gly Phe Glu Ala Val Gln Glu Val Pro Val Gly Leu
            1535            1540            1545

Val Gln Pro Ala Ser Ala Thr Leu Tyr Asp Tyr Tyr Asn Pro Glu
            1550            1555            1560

Arg Arg Cys Ser Val Phe Tyr Gly Ala Pro Ser Lys Ser Arg Leu
            1565            1570            1575

Leu Ala Thr Leu Cys Ser Ala Glu Val Cys Gln Cys Ala Glu Gly
            1580            1585            1590

Lys Cys Pro Arg Gln Arg Arg Ala Leu Glu Arg Gly Leu Gln Asp
            1595            1600            1605

Glu Asp Gly Tyr Arg Met Lys Phe Ala Cys Tyr Tyr Pro Arg Val
            1610            1615            1620
```

-continued

```
Glu Tyr Gly Phe Gln Val Lys Val Leu Arg Glu Asp Ser Arg Ala
    1625                1630                1635

Ala Phe Arg Leu Phe Glu Thr Lys Ile Thr Gln Val Leu His Phe
    1640                1645                1650

Thr Lys Asp Val Lys Ala Ala Asn Gln Met Arg Asn Phe Leu
    1655                1660                1665

Val Arg Ala Ser Cys Arg Leu Arg Leu Glu Pro Gly Lys Glu Tyr
    1670                1675                1680

Leu Ile Met Gly Leu Asp Gly Ala Thr Tyr Asp Leu Glu Gly His
    1685                1690                1695

Pro Gln Tyr Leu Leu Asp Ser Asn Ser Trp Ile Glu Glu Met Pro
    1700                1705                1710

Ser Glu Arg Leu Cys Arg Ser Thr Arg Gln Arg Ala Ala Cys Ala
    1715                1720                1725

Gln Leu Asn Asp Phe Leu Gln Glu Tyr Gly Thr Gln Gly Cys Gln
    1730                1735                1740

Val
```

<210> SEQ ID NO 12
<211> LENGTH: 5406
<212> TYPE: DNA
<213> ORGANISM: Homo sapiens

<400> SEQUENCE: 12

```
gaccagatca gcccccagag cagcctcatg gctggaggat ccaagagagg ttagatccgt      60
ctgtctgtct gctaccttct tcaccttatc tctgcagaag cccaggttgc tcttgttctc     120
tccttctgtg gttcatctgg gggtccccct atcggtgggg gtgcagctcc aggatgtgcc     180
ccgaggacag gtagtgaaag gatcagtgtt cctgagaaac ccatctcgta ataatgtccc     240
ctgctcccca aggtggact tcacccttag ctcagaaaga gacttcgcac tcctcagtct     300
ccaggtgccc ttgaaagatg cgaagagctg tggcctccat caactcctca gaggccctga     360
ggtccagctg gtggcccatt cgccatggct aaaggactct ctgtccagaa cgacaaacat     420
ccagggtatc aacctgctct tctcctctcg ccggggggcac ctcttttttgc agacggacca     480
gcccatttac aaccctggcc agcgggttcg gtaccgggtc tttgctctgg atcagaagat     540
gcgcccgagc actgacacca tcacagtcat ggtggagaac tctcacgcc tccgcgtgcg     600
gaagaaggag gtgtacatgc cctcgtccat cttccaggat gactttgtga tcccagacat     660
ctcagagcca gggacctgga gatctcagc ccgattctca gatggcctgg aatccaacag     720
cagcacccag tttgaggtga gaaatatgt ccttcccaac tttgaggtga gatcacccc      780
tggaaagccc tacatcctga cggtgccagg ccatcttgat gaaatgcagt tagacatcca     840
ggccaggtac atctatggga agccagtgca gggggtggca tatgtgcgct ttgggctcct     900
agatgaggat ggtaagaaga cttctctttcg ggggctggag agtcagacca agctggtgaa     960
tggacagagc cacatttccc tctcaaaggc agagttccag gacgccctgg agaagctgaa    1020
tatgggcatt actgacctcc aggggctgcg cctctacgtt gctgcagcca tcattgagtc    1080
tccaggtggg gagatggagg aggcagagct cacatcctgg tattttgtgt catctccctt    1140
ctccttggat cttagcaaga ccaagcgaca ccttgtgcct ggggcccct tcctgctgca    1200
ggccttggtc cgtgagatgt caggctcccc agcttctggc attcctgtca aagtttctgc    1260
cacggtgtct tctcctgggt ctgttcctga agcccaggac attcagcaaa acacagacgg    1320
gagcggccaa gtcagcattc caataattat ccctcagacc atctcagagc tgcagctctc    1380
```

```
agtatctgca ggctccccac atccagcgat agccaggctc actgtggcag ccccaccttc   1440
aggaggcccc gggtttctgt ctattgagcg gccggattct cgacctcctc gtgttgggga   1500
cactctgaac ctgaacttgc gagccgtggg cagtggggcc accttttctc attactacta   1560
catgatccta tcccgagggc agatcgtgtt catgaatcga gagcccaaga ggaccctgac   1620
ctcggtctcg gtgtttgtgg accatcacct ggcaccctcc ttctactttg tggccttcta   1680
ctaccatgga gaccacccag tggccaactc cctgcgagtg gatgtccagg ctggggcctg   1740
cgagggcaag ctggagctca gcgtggacgg tgccaagcag taccggaacg ggagtccgt    1800 gaagctccac ttagaaaccg actccctagc cctggtggcg ctgggagcct ggacacagc    1860 tctgtatgct gcaggcagca agtcccacaa gcccctcaac atgggcaagg tctttgaagc   1920
tatgaacagc tatgacctcg gctgtggtcc tggggggtgg gacagtgccc ttcaggtgtt   1980 ccagcagcg ggcctggcct tttctgatgg agaccagtgg accttatcca gaaagagact    2040
aagctgtccc aaggagaaga caacccggaa aaagagaaac gtgaacttcc aaaaggcgat   2100
taatgagaaa ttgggtcagt atgcttcccc gacagccaag cgctgctgcc aggatgggt    2160 gacacgtctg cccatgatgc gttcctgcga gcagcgggca gcccgcgtgc agcagccgga   2220
ctgccgggag cccttcctgt cctgctgcca atttgctgag agtctgcgca agaagagcag   2280
ggacaagggc caggcgggcc tccaacgagc cctggagatc ctgcaggagg aggacctgat   2340
tgatgaggat gacattcccg tgcgcagctt cttcccagag aactggctct ggagagtgga   2400
aacagtggac cgctttcaaa tattgacact gtggctcccc gactctctga ccacgtggga   2460
gatccatggc ctgagcctgt ccaaaaccaa aggcctatgt gtggccaccc cagtccagct   2520
ccgggtgttc cgcgagttcc acctgcacct ccgcctgccc atgtctgtcc gccgctttga   2580
gcagctggag ctgcggcctg tcctctataa ctacctggat aaaaacctga ctgtgagcgt   2640
ccacgtgtcc ccagtggagg ggctgtgcct ggctgggggc ggagggctgg cccagcaggt   2700
gctggtgcct gcgggctctg cccggcctgt tgccttctct gtggtgccca cggcagccgc   2760
cgctgtgtct ctgaaggtgg tggctcgagg gtccttcgaa ttccctgtgg gagatgcgt    2820 gtccaaggtt ctgcagattg agaaggaagg ggccatccat agagaggagc tggtctatga   2880
actcaacccc ttggaccacc gaggccggac cttggaaata cctggcaact ctgatcccaa   2940
tatgatccct gatggggact ttaacagcta cgtcagggtt acagcctcag atccattgga   3000
cactttaggc tctgaggggg ccttgtcacc aggaggcgtg gcctccctct tgaggcttcc   3060
tcgaggctgt ggggagcaaa ccatgatcta cttggctccg acactggctg cttcccgcta   3120
cctggacaag acagagcagt ggagcacact gcctcccgag accaaggacc acgccgtgga   3180
tctgatccga aaaggctaca tgcggatcca gcagtttcgg aaggcggatg ttcctatgc    3240 ggcttggttg tcacgggaca gcagcacctg gctcacagcc tttgtgttga aggtcctgag   3300 tttgcccag gagcaggtag gaggctcgcc tgagaaactg caggagacat ctaactggct    3360
tctgtcccag cagcaggctg acggctcgtt ccaggacccc tgtccagtgt tagacaggag   3420
catgcagggg ggtttggtgg caatgatgag gactgtggca ctcacagcct ttgtgaccat   3480
cgcccttcat catgggctgg ccgtcttcca ggatgagggt gcagagccat tgaagcagag   3540
agtggaagcc tccatctcaa aggcaaactc attttggggg agaaagcaa gtgctgggct    3600 cctgggtgcc cacgcagctg ccatcacggc ctatgccctg tcactgacca aggcgcctgt   3660
ggacctgctc ggtgttgccc acaacaacct catggcaatg gcccaggaga ctggagataa   3720
cctgtactgg ggctcagtca ctggttctca gagcaatgcc gtgtcgccca ccccggctcc   3780
```

-continued

```
tcgcaaccca tccgacccca tgccccaggc cccagccctg tggattgaaa ccacagccta  3840
cgccctgctg cacctcctgc ttcacgaggg caaagcagag atggcagacc aggcttcggc  3900
ctggctcacc cgtcagggca gcttccaagg gggattccgc agtacccaag acacggtgat  3960
tgccctggat gccctgtctg cctactggat tgcctcccac accactgagg agaggggtct  4020
caatgtgact ctcagctcca caggccggaa tgggttcaag tcccacgcgc tgcagctgaa  4080
caaccgccag attcgcggcc tggaggagga gctgcagttt tccttgggca gcaagatcaa  4140
tgtgaaggtg ggaggaaaca gcaaaggaac cctgaaggtc cttcgtacct acaatgtcct  4200
ggacatgaag aacacgacct gccaggacct acagatagaa gtgacagtca aaggccacgt  4260
cgagtacacg atggaagcaa acgaggacta tgagtacgat gagcttccag ccaaggatga  4320
cccagatgcc cctctgcagc ccgtgacacc cctgcagctg tttgagggtc ggaggaaccg  4380
ccgcaggagg gaggcgccca aggtggtgga ggagcaggag tccagggtgc actacaccgt  4440
gtgcatctgg cggaacggca aggtggggct gtctggcatg gccatcgcgg acgtcaccct  4500
cctgagtgga ttccacgccc tgcgtgctga cctggagaag ctgacctccc tctctgaccg  4560
ttacgtgagt cactttgaga ccgagggggcc ccacgtcctg ctgtattttg actcggtccc  4620
cacctcccgg gagtgcgtgg gctttgaggc tgtgcaggaa gtgccggtgg ggctggtgca  4680
gccggccagc gcaaccctgt acgactacta caaccccgag cgcagatgtt ctgtgtttta  4740
cggggcacca agtaagagca gactcttggc caccttgtgt tctgctgaag tctgccagtg  4800
tgctgagggg aagtgccctc gccagcgtcg cgccctggag cggggtctgc aggacgagga  4860
tggctacagg atgaagtttg cctgctacta ccccgtgtg gagtacggct tccaggttaa  4920
ggttctccga gaagacagca gagctgcttt ccgcctcttt gagaccaaga tcacccaagt  4980
cctgcacttc accaaggatg tcaaggccgc tgctaatcag atgcgcaact tcctggttcg  5040
agcctcctgc cgccttcgct tggaacctgg gaaagaatat ttgatcatgg gtctggatgg  5100
ggccacctat gacctcgagg gacaccccca gtacctgctg gactcgaata gctggatcga  5160
ggagatgccc tctgaacgcc tgtgccggag caccgccag cgggcagcct gtgcccagct  5220
caacgacttc ctccaggagt atggcactca ggggtgccag gtgtgagggc tgccctccca  5280
cctccgctgg gaggaacctg aacctgggaa ccatgaagct ggaagcactg ctgtgtccgc  5340
tttcatgaac acagcctggg accagggcat attaaaggct tttggcagca aagtgtcagt  5400
gttggc                                                             5406
```

DIAGNOSTIC COMPOSITION AND KIT FOR RENAL CELL CARCINOMA

CROSS-REFERENCE TO RELATED APPLICATION

This application is a U.S. National Phase application, under 35 U.S.C.§371, of International Application no. PCT/KR2008/004562, with an international filing date of Aug. 6, 2008, which is hereby incorporated by reference for all purposes.

TECHNICAL FIELD

The present invention relates to a composition and a kit for diagnosing renal cell carcinoma.

BACKGROUND ART

Tumors that develop in the kidney include renal cell carcinoma (in adults), Wilms tumor (in children) and uncommonly sarcoma.

Kidney cancer can be diagnosed through evaluation of imaging and biochemical tests. Imaging methods include computed tomography (CT) scanning and angiography. Biochemical evaluation involves using a probe such as an antibody that binds specifically to a diagnostic marker, which is a kidney cancer-specific protein or gene that is up- or down-regulated specifically in the tissues of kidney cancer.

Many biochemical diagnostic methods based on using a kidney cancer-specific mRNA or protein have been developed to detect renal cell carcinoma. For example, International Pat. Publication No. WO2005/024603 employs the differential expression of a gene between normal and tumor tissues. Lein, M. et al. suggested that MMP-2, which is overexpressed in kidney cancer, may be useful as a diagnostic marker of kidney cancer (International Journal of Cancer, 2000, Vol. 85, p 801-804). Also, TNFRSF7, which is expressed at high levels when renal function is abnormal, has the potential as a diagnostic marker for kidney cancer (Nakatsuji, T., Clinical and Exprerimental Medicine, 2003, Vol. 2, p 192-196). Other proteins which are overexpressed by kidney cancer and thus useful as diagnostic markers of kidney cancer, include MCM3AP (JP Pat. Publication No. 2005-520536), KRT19 (JP Pat. Publication No. 2005-507997), SLK4 (WO2002/06339), FGF2 (Miyake, H. et al., 1996, Cancer Research, Vol. 56, p 2440-2445), MMP14 (Kitagawa, Y., 1999, Journal of Urology, Vol. 162, p 905-909), and ERBB2 (Freeman, M. R., 1989, Cancer Research, Vol. 49, p 6221-6225). Further, International Pat. Publication Nos. WO2006/099485A2 and WO2003/046581 and U.S. Pat. Publication No. 2006/0183120A1 disclose methods of diagnosing kidney cancer based on using specific diagnostic markers.

The present invention has been completed based on using proteins specific to renal cell carcinoma as diagnostic markers therefor.

DISCLOSURE

[Technical Problem]

It is therefore an object of the present invention to provide a composition for diagnosing renal cell carcinoma.

It is another object of the present invention to provide a kit for diagnosing renal cell carcinoma.

It is a further object of the present invention to provide a method of screening a therapeutic agent for renal cell carcinoma.

It is yet another object of the present invention to provide a method of screening a substance that causes renal cell carcinoma.

[Technical Solution]

In one aspect, the present invention relates to a composition for diagnosing renal cell carcinoma.

The composition for diagnosing renal cell carcinoma includes an antibody binding specifically to nicotinamide N-methyltransferase (NNMT), L-plastin, secretagogin (SCGN), NM23A, CapG, which is an actin regulatory protein, and/or C4aANA, which is a fragment that is released from the C4 complement by protelytic cleavage and have an anaphylatoxin part.

Nicotinamide N-methyltransferase (NNMT) is an enzyme that catalyzes the N-methylation of nicotinamide. It has rarely been known to have an association with cancer. The enzyme consists of 264 amino acids (see, SEQ ID No. 1 for the amino acid sequence thereof and SEQ ID No. 2 for the nucleotide sequence thereof), and has a molecular weight of 29.6 kDa. Two-dimensional electrophoresis analysis according to the present invention revealed that the enzyme has an isoelectric point (pI) of 5.12 and a molecular weight of 29.2 kDa. The nucleotide and amino acid sequences thereof are disclosed herein, and also can be located in the Genbank database (Gene ID: U08021.1) and the Swiss-PROT database (Swiss-PROT: P40261&U08021).

Plastins belong to a subclass of actin-binding proteins. Two major isoforms have been characterized: T-plastin and L-plastin. L-plastin (also known as LCP-1) is present predominantly in hematopoietic cells, but has also been found in diverse types of tumor cells during carcinogenesis. It has not been known if L-plastin is involved in kidney cancer. It consists of 627 amino acids (see, SEQ ID No. 3 for the amino acid sequence thereof and SEQ ID No. 4 for the nucleotide sequence thereof), and has a molecular weight of 70.8 kDa. Two-dimensional electrophoresis analysis according to the present invention revealed that L-plastin has an isoelectric point (pI) of 4.83 and a molecular weight of 67.03 kDa. The nucleotide and amino acid sequences of L-plastin are disclosed herein, and also can be located in the Genbank database (Gene ID: M22300) and the Swiss-PROT database (Swiss-PROT: P13796).

Secretagogin (SCGN) is expressed predominantly in the pancreas, yet also at low levels in other tissues. It has also been found in sera from patients having cerebral ischemia. It consists of 276 amino acids (see, SEQ ID No. 5 for the amino acid sequence thereof and SEQ ID No. 6 for the nucleotide sequence thereof), and has a molecular weight of 32.2 kDa. Two-dimensional electrophoresis analysis according to the present invention revealed that SCGN has an isoelectric point (pI) of 4.68 and a molecular weight of 32.5 kDa. A recent report showed that SCGN is differentially expressed in tumors of the human brain (APMIS, 2007 April, 115(4):319-26). The nucleotide and amino acid sequences of SCGN are disclosed herein, and also can be located in the Genbank database (Gene ID: Y16752) and the Swiss-PROT database (Swiss-PROT: O76038).

NM23 genes exhibit reduced mRNA expression levels in metastatic tumor cells. A NM23 gene encodes a polypeptide that consists of 152 amino acids (see, SEQ ID No. 7 for the amino acid sequence thereof and SEQ ID No. 8 for the nucleotide sequence thereof) which has a predicted molecular weight of 16.9 kDa. Two-dimensional electrophoresis analysis according to the present invention revealed that the NM23A protein has a pI of 5.8 and a molecular weight of 17.3 kDa. The inventors of this application found that NM23A is highly expressed in kidney tumor tissues. The nucleotide and amino acid sequences of NM23A are disclosed herein, and also can be located in the Genbank database (Gene ID: NM_198175 & NP_937818).

The actin regulatory protein CapG reversibly blocks the barbed ends of actin filaments, and plays an important role in regulating cytoplasmic and nuclear structures. The CapG protein is overexpressed in pancreatic cancer (Gut. 2007 January, 56(1):95-106, Epub 2006 Jul. 17) and in oral squamous cell carcinoma (BMC Cancer. 2008 Feb. 1, 8:39). CapG overexpression has been recently reported to affect the motility and spread of tumor cells. The CapG protein consists of 238 amino acids (see, SEQ ID No. 9 for the amino acid sequence thereof and SEQ ID No. 10 for the nucleotide sequence thereof). Two-dimensional electrophoresis analysis according to the present invention revealed that the CapG protein has a pI of 6.3 and a molecular weight of 40.6 kDa. The nucleotide and amino acid sequences of CapG are disclosed herein, and also can be located in the Genbank database (Gene ID: U12026) and the Swiss-PROT database (Swiss-PROT: P40121).

C4aANA is an activation peptide that is released from the complement C4, mediating local inflammatory reactions in the blood, through cleavage of the complement C4 and possesses anaphylatoxin activity. Renal cell carcinoma patients show increased plasma levels of C4aANA. The C4aANA is a peptide fragment of 245 amino acids, which correspond to a sequence spanning positions from 710 to 945 of complement C4-A precursor (Swiss-PROT: P0C0L4; see, SEQ ID No. 11 for the amino acid sequence thereof and SEQ ID No. 12 for the nucleotide sequence thereof). There has been no report describing that the peptide is present at elevated levels in kidney cancer and other types of cancer. The nucleotide and amino acid sequences of C4aANA are disclosed herein, and also can be located in the Swiss-PROT database (Swiss-PROT: P0C0L4 & K02403).

The aforementioned proteins are referred herein to as "renal cell carcinoma markers" for convenience.

As is described in the below examples, the renal cell carcinoma marker proteins are expressed in renal cell carcinoma patients, or are expressed at higher levels than those in kidney tissues of normal individuals or in normal tissues of the kidney.

The composition for diagnosing renal cell carcinoma according to the present invention may be directly or indirectly used to identify renal cell carcinoma development and to monitor renal cell carcinoma progression and/or response to its treatment.

The present composition may include a single antibody against a single renal cell carcinoma marker, or may include a mixture of different antibodies against two or more renal cell carcinoma markers. The composition may be in any form of a freeze-dried solid or a solution such as aqueous solutions or buffers.

The composition for diagnosing renal cell carcinoma according to the present invention may be used to detect the expression of renal cell carcinoma markers described above, through being brought into contact with a biological sample and then drawing a comparison of expression levels therein with those in a normal kidney tissue or a kidney tissue from a normal individual.

When the marker expression level is higher than the normal level, a subject is diagnosed with renal cell carcinoma, wherein the normal level may be calculated from the mean value of measured expression levels of a renal cell carcinoma marker in samples from several healthy individuals and/or samples from several individuals having a kidney cancer).

The term "biological sample" as used herein, refers to a sample that is collected from a subject who exhibits a different expression level of a renal cell carcinoma marker as described above, as compared to an expression level of a normal control sample. The expression level varies according to the development or progression of renal cell carcinoma. Examples of the biological samples include kidney tissues, cancerous kidney tissues, cells derived from such tissues, and bodily fluid samples such as whole blood, plasma and serum samples.

The term "specifically bind," as used herein, means that an antibody forms an antigen-antibody complex with an antigen protein thereof, that is, a renal cell carcinoma marker, but does not substantially form such a complex with other proteins. The term "substantially," as used herein, means that nonspecific complex formation may occur even at low levels. In other words, the term "specifically bind" can be expressed as binding determined by a specific structure of an antigen protein, that is, the antigenic determinant of the antigen, epitope.

The term "epitope", as used herein, is meant to indicate a portion of a renal cell carcinoma marker as described above that defines an antigenic determinant, i.e. which possesses antigenicity or immunogenicity. An epitope typically consists of at least ten amino acids. The epitope can be identified using any epitope analysis method known in the art, such as phage display or reverse immunogenetics.

The term "antibody", as used herein, is meant to include all forms of a molecule capable of binding specifically to a renal cell carcinoma marker according to the present invention. Thus, the antibody includes monoclonal antibodies, polyclonal antibodies, multispecific antibodies (which recognize two or more antigens or epitopes; e.g., bispecific antibodies), as well as fragments of an antibody molecule, recombinant antibodies and chemically modified antibodies, which retain an ability to specifically bind to any one of the renal cell carcinoma diagnostic markers of the present invention. Examples of antibody fragments include Fab, F(ab')$_2$, single chain Fv (scFv; consisting of a variable heavy (VH) chain and a variable light (VL) chain connected by an appropriate linker), Fv, and Fab/c (having one Fab and a complete Fc). The antibody fragments may be obtained by treating a whole antibody with a proteolytic enzyme, such as papain or pepsin, or by introducing a gene encoding an antibody fragment into host cells using a recombinant DNA technique as described below and expressing the gene in the host cells. The immunoglobulin isotypes of the above antibodies are not specifically limited as long as they retain the ability to bind specifically to a renal cell carcinoma diagnostic marker according to the present invention, and may be any one of IgG, IgM, IgA, IgE and IgD.

The expression levels of renal cell carcinoma markers in biological samples may be evaluated through the specific binding of the above antibodies to an antigen present in the samples. The antigen-antibody complexes may be quantitatively and/or qualitatively analyzed using various immunological analytic methods known in the art, such as enzyme immunoassay, fluorescent immunoassay, radioimmunoassay, and luminescent immunoassay. The quantitative and qualitative analysis allows the identification of renal cell carcinoma development and the monitoring of renal cell carcinoma progression and response to treatment.

The enzyme immunoassay may be performed out using peroxidase (POD), alkaline phosphatase, β-galactosidase, urease, catalase, glucose oxidase, lactate dehydrogenase, amylase, a biotin-avidin complex, or the like. The fluorescent immunoassay may be performed out using a fluorescent substance or a fluorophore, such as fluorescein isothiocyanate, tetramethylrhodamine isothiocyanate, substituted rhodamine isothiocyanate, dichlorotriazine isothiocyanate, Alexa, or AlexaFluoro. Examples of radioisotopes useful for the radioimmunoassay include tritium, iodine ($^{131}$I, $^{125}$I, $^{123}$I, and $^{121}$I), phosphorous ($^{32}$P), sulfur ($^{35}$S), and metals (e.g., $^{68}$Ga, $^{67}$Ga, $^{68}$Ge, $^{54}$Mn, $^{99}$Mo, $^{99}$Tc, $^{133}$Xe, etc.). The luminescent immunoassay may be carried out with a luciferase system, a luminol-hydrogen peroxide-POD system, a dioxetane compound system, or the like.

When an avidin-biotin system or a streptavidin-biotin system is used, a label may be bound to an antibody according to the intended use. For the enzyme immunoassay, the conjugation of a label to an antibody may be carried out using a glutaraldehyde method, a maleimide method, a pyridyl disulfide method, or a periodic acid method. In the radioimmunoassay, a chloramine-T method or a Bolton-Hunter method may be used.

In addition to the above four methods, immunological analysis may be carried out using immunoprecipitation, turbidimetric immunoassay, Western blotting, immunostaining, and immunodiffusion. However, immunological analysis is preferably performed using the aforementioned four methods, more preferably an enzyme immunoassay, and most preferably an enzyme-linked immunosorbent assay (ELISA).

The diagnostic accuracy of an immunological analytic method for renal cell carcinoma may be assessed through receiver operating characteristic (ROC) analysis. The area under the curve (AUC) is used as a measure of accuracy. ROC analysis is a representative way to discriminate sensitivity and specificity (Zweig, M. H., and Campbell, G., Clin. Chem. 39 (1993) 561-577). The area under the receiver operating characteristic (ROC) curve (AUC) may take values between 0.5 and 1, in which 0.5 indicates that there is no difference between a patient and a normal individual and thus the patient is not discriminated with the normal individual, and 1 indicates perfect discrimination between a patient and a normal individual.

A polyclonal antibody may be prepared by immunizing an animal, such as birds (e.g., chickens, etc.) or mammals (e.g., rabbits, goats, horse, sheep, rats, etc.), with a renal cell carcinoma diagnostic marker according to the present invention. The antibody may be purified from the blood of the immunized animal using a method known in the art, such as ion-exchange chromatography and affinity chromatography.

A monoclonal antibody may be obtained by establishing a hybridoma cell line, which secretes a monoclonal antibody specific to a renal cell carcinoma diagnostic marker according to the present invention. A hybridoma cell line may be produced by immunizing an animal (e.g., mice) with a renal cell carcinoma diagnostic marker according to the present invention, extracting splenocytes from the immunized animal, fusing the splenocytes with a myeloma cell line to produce hybridoma cells from the fused cells, and identifying a hybridoma cell line producing a desired monoclonal antibody. The monoclonal antibody is then recovered from the hybridoma cells using a method known in the art.

The antibody of the present invention, as described above, is not particularly limited as long as it is able to bind specifically to the diagnostic marker of renal cell carcinoma according to the present invention, but is preferably a monoclonal antibody.

In this regard, the preparation of the monoclonal antibody of the present invention will be described below in further detail.

An immunogen, which is the renal cell carcinoma diagnostic marker of the present invention, is administered to a mammal, such as rats, mice, rabbits, monkeys and goats. The dose of the immunogen may be suitably determined taking into accounts the type of an animal to be immunized, administration route, and the like, by those skilled in the art. The dose typically ranges from about 50 to 200 μg per animal. An immunogen is typically diluted or suspended in an appropriate amount of phosphate-buffered saline (PBS) or physiological saline, emulsified with a common adjuvant, and injected subcutaneously or intraperitoneally. After the first injection, boost immunization may be performed preferably 2 to 10 times, preferably 3 to 4 times, at intervals of several days to several weeks, preferably at intervals of 1 to 4 weeks. During the immunization period, the antibody titer of sera from the immunized animal is measured, for example, using ELISA. When the antibody titer reaches a plateau, the immunogen is finally injected intravenously or intraperitoneally. Antibody-producing cells are collected two to five days after the final immunization. Examples of antibody-producing cells include splenocytes (spleen cells), lymph node cells, and peripheral blood cells. Spleen cells or lymph node cells are preferred.

After antibody-producing cells are collected, hybridoma cell lines that secrete monoclonal antibodies specific to the administered immunogen, that is, the renal cell carcinoma diagnostic marker of the present invention, are produced and identified using a technique known in the art. Hybridomas may be typically established by extracting splenocytes from the immunized animal, fusing the splenocytes with a myeloma cell line to produce hybridoma cells, and identifying a hybridoma cell line producing a monoclonal antibody binding specifically to the immunogen. Myeloma cell lines to be fused with antibody-producing cells may be commercially available cell lines derived from animals, such as mice. Preferably, myeloma cell lines are derived from an animal of the same species as an animal to be immunized. They also have drug selectivity. In other words, they cannot survive in an HAT selection medium supplemented with hypoxanthine, aminopterin and thymidine in a state of being not used with splenocytes, but can survive in a state of being fused with splenocytes. Examples of myeloma cell lines include a P3X63 strain (ATCC TIB9), which is a BALC/c mouse-derived hypoxanthine guanine phosphoribosyl-transferase (HGPRT)-deficient cell line.

The myeloma cell lines are then fused with splenocytes that are antibody-producing cells. Cell fusion is performed in a serum-free medium for animal cell culture, such as DMEM or RPMI-1640, by mixing the antibody-producing cells with the myeloma cell lines at a proper ratio (about 1:1 to 20:1) in the presence of a cell fusion stimulator. The cell fusion stimulator, such as polyethylene glycol having an average molecular weight of 1,500 to 4,000 daltons, may be used at a concentration of about 10-80%. Also, an auxiliary agent, such as dimethylsulfoxide, may be used in combination in order to increase fusion efficiency. Further, the cell fusion may be achieved using a commercially available cell fusion device.

After the cell fusion is completed, desired hybridomas are selected. In general, the cell suspension is properly diluted, for example, in a fetal bovine serum-containing RPMI-1640 medium. Cells are then aliquotted into a microtiter plate at a density of about two million cells per well, and a selection medium is added to each well. Thereafter, the cells are cultured at 20-40° C. The medium is exchanged with the same fresh medium. When the myeloma cell line is an HGPRT-deficient strain or a thymidine kinase-deficient strain, only hybridomas of antibody-producing cells and myeloma cell lines are selectively cultured and propagated in a selection medium supplemented with hypoxanthine, aminopterin and thymidine (HAT medium). Cells surviving for about 14 days in the selection medium are obtained as hybridomas.

Subsequently, the supernatant of the hybridoma culture is screened for the presence of a desired antibody. The screening of hybridomas may be carried out using a method known in the art. For example, an enzyme immunoassay (EIA) or ELISA, or a radioimmunoassay may be used. The fused cells are cloned, for example, using a limiting dilution method.

A cloned hybridoma is grown in an animal cell culture medium, such as 10% FBS-containing RPMI-1640, EMEM, or a serum-free medium, under general culture conditions (e.g., 37° C., 5% $CO_2$), for a period of about 2 to 10 days. A desired monoclonal antibody may be obtained from the supernatant of the culture.

Monoclonal antibodies may be recovered using a technique known in the art. For example, a salting-out method using ammonium sulfate, ion-exchange chromatography, affinity chromatography and gel filtration chromatography may be used, and the methods may be used singly or in combination.

As well, the monoclonal antibodies of the present invention may be produced using a recombinant DNA technique, which includes cloning an antibody gene from a hybridoma, inserting the antibody gene into a suitable vector, introducing the vector into a suitable host cell, and expressing the antibody gene in the host cell (Vandamme, A. M. et al., Eur. J. Biochem., 192, 767-775, 1990).

In detail, an mRNA encoding a variable region of an antibody according to the present invention is isolated from a hybridoma producing the antibody of the present invention. The mRNA isolation is performed using a method known in the art. For example, total RNA is isolated using guanidine ultracentrifugation (Chirgwin, J. M. et al., Biochemistry Vol 18, 5294-5299, 1979), an AGPC method (Chomczynski, P. et al., Anal. Biochem., 162, 156-159), or the like. Then, a desired mRNA is purified from the total RNA, for example, using an mRNA Purification Kit (Pharmacia). Alternatively, mRNA can be directly obtained using a QuickPrep mRNA Purification Kit (Pharmacia).

A cDNA coding for a variable (V) region of an antibody may be synthesized from the obtained mRNA using a reverse transcriptase. If desired, RACE PCR may be used for synthesis and amplification of cDNA. The cDNA thus obtained, encoding the variable region, is inserted into an expression vector that carries a DNA sequence encoding a constant (C) region of an antibody. The expression vector, as described below with respect to the production of genes of the renal cell carcinoma markers of the present invention using a recombinant DNA technique, may contain a regulatory region, such as a promoter, an enhancer, a replication origin, a polyadenylation signal, and a ribosome-binding site. The expression vector is transformed into a host cell, in which the antibody is expressed. The antibody gene may be expressed by separately inserting a DNA sequence encoding a heavy (H) chain or a light (L) chain of the antibody into an expression vector and co-transforming the vectors into a host cell, or by inserting DNA sequences encoding an H chain and an L chain into a single expression vector and transforming the vector into a host cell (WO94/11523).

The renal cell carcinoma markers of the present invention, as immunogens used to obtain the antibodies of the present invention, may be constructed using a recombinant DNA technique known in the art. Typically, a cDNA of a renal cell carcinoma marker according to the present invention is prepared, inserted into an expression vector, and transformed into a prokaryotic or eukaryotic host cell, which is cultured in a proper medium. A desired renal cell carcinoma marker is obtained form the transformed cell or the medium of the culture. The cDNA may be constructed within the capacity of those skilled in the art based on a gene sequence searchable from nucleotide/protein database or the sequence disclosed herein.

The cDNA may be prepared through phosphoamidite-based DNA synthesis, RT-PCR, hybridization for obtaining a desired cDNA from a cDNA library, or the like. If desired, a desired cDNA sequence may be amplified, for example, using PCR.

The expression vector is commercially available from Novagen, Takara Shuzo, Qiagen, Stratagene, Promega, Roche Diagnositics, Invitrogen, Genetics Institute, and the like.

The expression vector may include, in addition to a DNA sequence encoding a renal cell carcinoma diagnostic marker according to the present invention, regulatory elements, such as a promoter, an enhancer, a polyadenylation signal, a ribosome-binding site, a replication origin, a terminator, and a selection marker. In order to facilitate protein isolation and purification, the vector may also include a purification tag peptide sequence (peptide label), such as a histidine repeat.

Host cells suitable for use in the present invention include prokaryotic cells (e.g., *E. coli* or *Bacillus subtilis*), and eukaryotic cells, such as yeast (e.g., *Saccharomyces cerevisiae*), insect cells (e.g., Sf cells), and mammalian cells (e.g., COS, CHO, BHK).

The renal cell carcinoma markers of the present invention may be purified from host cells or cultures thereof through ultrafiltration, gel filtration, ion-exchange chrmomatography, affinity chromatography (useful when a peptide label is bound to a polypeptide to be purified), HPLC, hydrophobic chromatography, and isoelectric chromatography. If desired, the methods are used in combination.

The production of the renal cell carcinoma markers of the present invention using a recombinant DNA technique may be achieved as disclosed herein, as well as in Sambrook et al., Molecular Cloning, A Laboratory Mannual, Cold Spring Harbor Laboratory Press, US (1989); Ausubel et al., Current Protocols in Molecular Biology, Jon Willey & Sons, US (1993); Sambrook, J. & Russel, D., Molecular Cloning, A Laboratory Mannual, Cold Spring Harbor Laboratory Press, January 15, 2001, Vol. 1: 7.42 to 7.45, Vol. 2: 8.9 to 8.17; and the like. The above literatures are considered as a portion of this specification.

A fragment of a renal cell carcinoma marker according to the present invention may be used as an immunogen for producing an antibody against the renal cell carcinoma marker. The antibody obtained using the fragment retains also the ability to bind specifically to the renal cell carcinoma marker of the present invention.

In another aspect, the present invention relates to a kit for diagnosing renal cell carcinoma.

The diagnostic kit for renal cell carcinoma includes an antibody binding specifically to a renal cell carcinoma marker according to the present invention.

The antibody included in the diagnostic kit of the present invention may be present singly or in the form of a mixture, or may be conjugated to a solid-phase carrier or be in a free form.

The present kit may include a secondary antibody used in an immunoassay for the quantitative or qualitative detection of the expression level of the renal cell carcinoma marker (e.g., a renal cell carcinoma marker-specific antibody labeled with a fluorescein capable of detecting the expression level of the renal cell carcinoma marker), a carrier, a washing buffer, a sample dilution buffer, an enzyme substrate, a reaction stop buffer, and the like.

The present kit may preferably include a guide book through the use of which the development or improvement of renal cell carcinoma can be determined from quantitatively or qualitatively detected expression levels of the renal cell carcinoma marker.

In a further aspect, the present invention relates to a method of screening a therapeutic agent for renal cell carcinoma.

The screening method of the present invention includes bringing a substance to be tested into contact with a renal cell carcinoma line or a renal cell carcinoma tissue, and detecting the substance to reduce expression of a renal cell carcinoma marker in the renal cell carcinoma line or the renal cell carcinoma tissue by comparing states of being contacted with and not being contacted with the test substance. The screening may be carried out using an in vivo system, for example, rats having induced renal cell carcinoma, or using an in vitro culture of a renal cell carcinoma line or a renal cell carcinoma tissue.

In a yet another aspect, the present invention relates to a method of screening for a substance that causes renal cell carcinoma.

The screening method for a substance causing renal cell carcinoma includes bringing a substance to be tested into contact with a normal kidney cell line or a normal kidney tissue, and detecting the substance to increase expression of a renal cell carcinoma marker according to the present invention in the normal kidney cell line or the normal kidney tissue by comparing states of being contacted with and not being contacted with the test substance. This screening may also be carried out either in vivo or in vitro.

In another aspect, a kidney carcinoma cell line or a cancerous kidney tissue may also be employed in the screening method of a substance causing renal cell carcinoma. In this case, the method includes bringing a substance to be tested into contact with a renal carcinoma line or a renal cell carcinoma tissue; and detecting the substance to increase expression of a renal cell carcinoma marker according to the present invention in the renal carcinoma line or the renal cell carcinoma tissue by comparing states of being contacted with and not being contacted with the test substance. This screening may also be carried out either in vivo or in vitro.

The description about the composition for diagnosing renal cell carcinoma is also applicable to the diagnostic kit for renal cell carcinoma, the method of screening a therapeutic agent for renal cell carcinoma, and the method of screening a substance causing renal cell carcinoma.

[Advantageous Effects]

In accordance with the present invention, the composition and kit of the present invention are useful for the detection of renal cell carcinoma and for purposes of arriving at a renal cell carcinoma diagnosis.

BEST MODE FOR INVENTION

Figure 1:
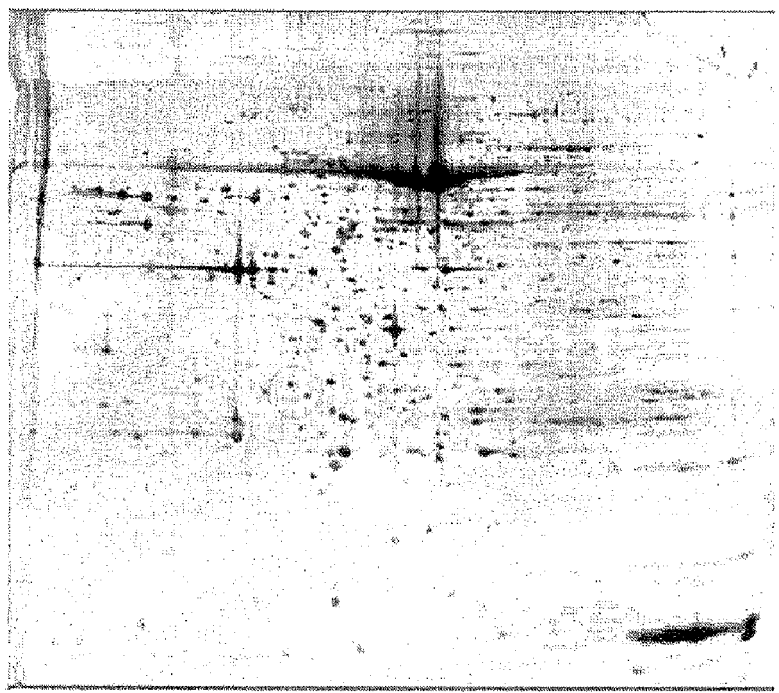
FIG. 1 is a 2D gel image of a normal kidney tissue from a renal cell carcinoma patient.

A better understanding of the present invention may be obtained through the following examples which are set forth to illustrate, but are not to be construed as limiting the present invention.

EXAMPLE 1

Identification of Protein Markers for Renal Cell Carcinoma 1-1. Preparation of Kidney Tissue Samples from Normal Individuals and Patients In order to investigate expression patterns of renal cell carcinoma-specific proteins, kidney tissue samples were collected from patients afflicted with renal cell carcinoma.

From 13 renal cell carcinoma patients, a total of 13 cancerous tissue samples were collected. Also, 13 normal kidney tissue samples were collected from regions adjacent to cancer.

Blood samples also were collected from renal cell carcinoma patients and normal individuals to obtain plasmas therefrom.

The normal and cancerous tissues of the kidney were homogenized and centrifuged, and membrane fractions were recovered. In brief, 200 mg of kidney cancerous tissue was homogenized in 1 ml of a protein extraction buffer (50 mM Tris-HCl, pH 7.5, 100 mM NaCl, 1 mM benzamidin) using a homogenizer (Powergen 125, Fisher Scientific, Germany), and centrifuged at 12,000×g for 1 hr. After the supernatant was discarded, an insoluble membrane fraction was recovered.

The patients donating the tissue samples were afflicted with any one of three types of renal cell carcinoma, namely clear-cell renal cell carcinoma (RCC), papillary RCC or chromophobe RCC. Each type of renal cell carcinoma was graded according to cancer progression (size of cancer masses) into stages 1 to 4 (grade 1 (one patient)), grade 2 (two patients), grade 3 (six patients), and grade 4 (four patients).

1-2. Preparation of Protein Samples for Two-Dimensional Gel Electrophoresis

Clear-cell RCC tissues, stored at −80° C. until use, were partially cut out to obtain 200 mg of tissue using a surgical knife. 200 mg of the kidney cancerous tissue was homogenized in 0.6 ml of a protein extraction buffer for two-dimensional electrophoresis (2-DE) (7 M urea, 2 M thiourea, 4% (w/v) 3-[(3-cholamidopropyl)dimethylammonio])-1-propanesulfonate (CHAPS), 1% (w/v) dithiothreitol (DTT), 2% (v/v) pharmalyte, 1 mM benzamidine) using a mechanical homogenizer (Powergen 125, Fisher Scientific, Germany). The tissue homogenate was agitated at a rapid speed for 1 hr so as to solubilize proteins, and centrifuged at 12,000×g for 1 hr. The resulting supernatant was recovered and used in two-dimensional electrophoresis.

Normal kidney tissues were prepared according to the same procedure as described above.

Plasmas were incubated in a 1/40 volume of a protein extraction buffer for 2-DE (7 M urea, 2 M thiourea, 4% CHAPS, 1% DTT, 2% pharmalyte, 1 mM benzamidine) with agitation at a rapid speed for 1 hr, and centrifuged at 12,000×g for 1 hr. The resulting supernatant, in which proteins were solubilized, was recovered and used in two-dimensional gel electrophoresis.

The membrane fraction samples from normal and cancerous kidney tissues were incubated in 0.2 ml of a protein extraction buffer for 2-DE (7 M urea, 2 M thiourea, 4% CHAPS, 1% DTT, 2% pharmalyte, 1 mM benzamidine) with agitation at a rapid speed for 30 min at room temperature, and centrifuged at 12,000×g. The resulting supernatant, in which proteins were solubilized, was recovered and used in two-dimensional electrophoresis.

1-3. Two-Dimensional Electrophoresis

For isoelectric focusing (IEF) as the first dimension, 0.6 ml of a reswelling solution (7 M urea, 2 M thiourea, 2% CHAPS, 1% DTT, 1% pharmalyte) was added to grooves of a DryStrip Reswelling Tray, and a 24 cm-long DryStrip ranging from pH 4 to 10 (Genomine, Inc., Pohang, Korea) was placed into the groove of the tray and allowed to be rehydrated therein for about 12-16 hrs at room temperature.

0.05 ml (0.2 mg protein) of each tissue sample, 0.08 ml (0.2 mg protein) of each plasma sample, and 0.08 ml (0.2 mg protein) of each membrane fraction sample were loaded onto the rehydrated strip. Then, IEF was carried out at 20° C. with a Multiphore II system (Amersham Biosciences) according to the user manual provided by the manufacturer. Separation was performed under voltage conditions of 150 V to 3,500 V in 3 hrs and 3,500 V for 26 hrs to reach a total of 96 kVh.

Then, the first-dimension gels were subjected to second-dimension separation (SDS-PAGE). Each gel strip was equilibrated for 10 min in a first equilibration buffer (50 mM Tris-HCl, pH 6.8, 6 M urea, 2% SDS, 30% glycerol, 1% DTT), and was subsequently further equilibrated in a second equilibration buffer (50 mM Tris-HCl, pH 6.8, 6 M urea, 2% SDS, 30% glycerol, 2.5% iodoacetamide). The equilibrated strip was positioned on top of a SDS-PAGE gel (20×24 cm, 10-16% gradient), which was run at 20° C. to reach a total of 1.7 kVh using a Hoefer DALT 2D system (Amersham Biosciences).

In order to visualize proteins, the second-dimension gel was silver-stained according to a method described in Oakley et al., Anal. Biochem. 1980, 105:361-363). In brief, after the second-dimension electrophoresis, the gel was incubated in a fixing solution (40% ethanol, 10% acetic acid) for 1 hr with agitation, and then incubated three times in a rehydration solution (5% ethanol, 5% acetic acid) for 30 min each time with agitation. The gel was then washed with tertiary distilled water three times for 30 min each time, and subjected to silver staining. The gel was stained through agitation in a silver staining solution (0.8% silver nitrate, 1.4% ammonia solution (25%), 0.2% 10N NaOH) for 50 min, and washed with tertiary distilled water four times for 4 min each. The washed gel was developed with a development solution (0.1% formaldehyde solution (37%), 0.01% citric acid). When a desired density of staining was achieved, the development was terminated with a rehydration solution (5% ethanol, 5% acetic acid). The silver-stained gels were scanned using an image scanner (Duoscan T1200 scanner, AGFA, Germany), and the resulting two-dimensional gel (2D gel) images are shown in FIGS. 1 to 6.

Figure 2:
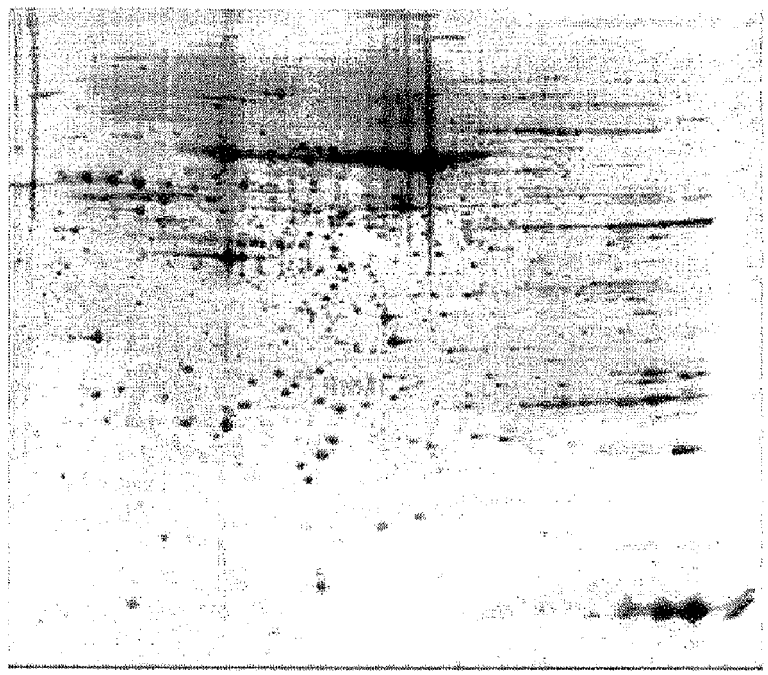
FIG. 2 is a 2D gel image of a cancerous kidney tissue from a renal cell carcinoma patient.
Figure 3:
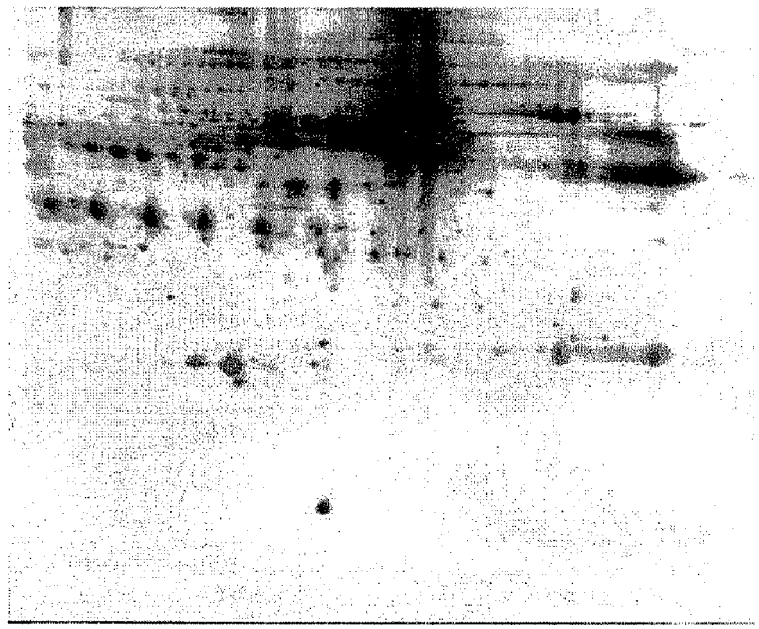
FIG. 3 is a 2D gel image of a serum sample from a normal individual.
Figure 4:
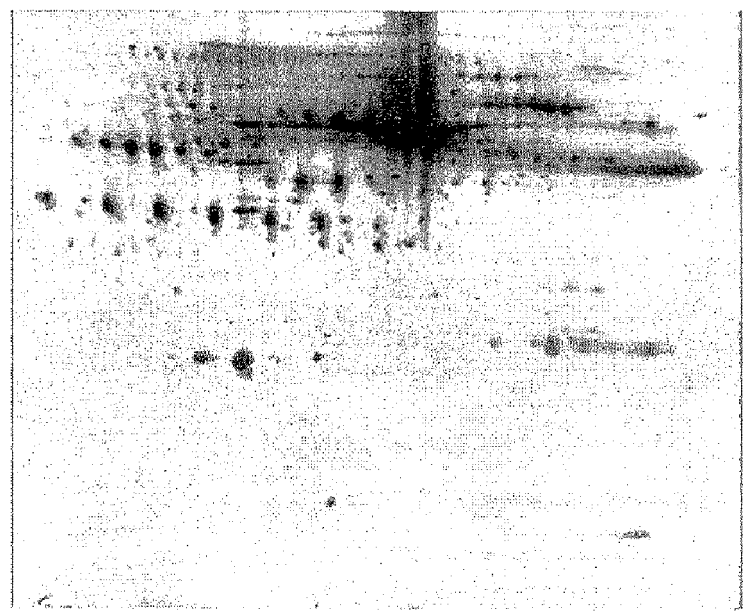
FIG. 4 is a 2D gel image of a serum sample from a renal cell carcinoma patient.
Figure 5:
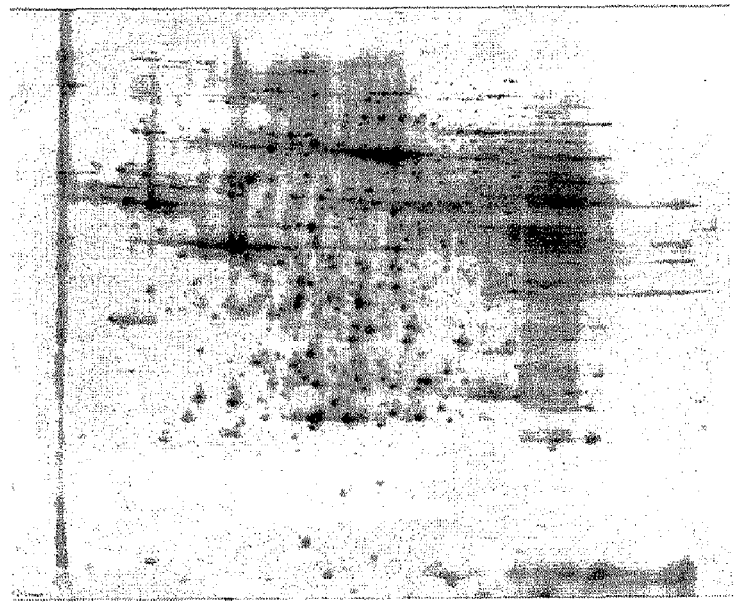
FIG. 5 is a 2D gel image of a membrane fraction sample from a normal kidney tissue.
Figure 6:
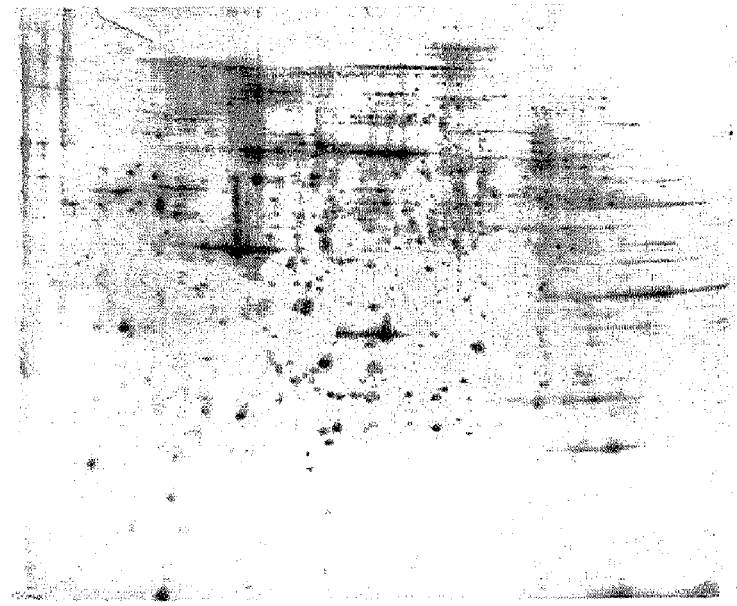
FIG. 6 is a 2D gel image of a membrane fraction sample from cancerous kidney tissue.

FIG. 1 is a representative 2D gel image of a normal kidney tissue from a renal cell carcinoma patient, and FIG. 2 is a representative 2D gel image of a cancerous kidney tissue from a renal cell carcinoma patient. FIG. 3 is a representative 2D gel image of a serum sample from a normal individual, and FIG. 4 is a representative 2D gel image of a serum sample from a renal cell carcinoma patient. FIG. 5 is a representative 2D gel image of a membrane fraction sample from a normal kidney tissue, and FIG. 6 is a representative 2D gel image of a membrane fraction sample from a cancerous kidney tissue.

1-4. Comparative Analysis of Two-dimensional Images

The scanned gel images were compared with each other to assess the differential expression of proteins. The quantitative comparison of protein spots in the gel images was performed using a PDQest software (version 7.0, BioRad). The quantity of each protein spot was normalized by total intensity of valid spots. Protein spots were selected as significant expression variations when their expression levels were 2-fold or higher compared to a control sample.

A total of 120 protein spots were selected as candidate markers, and were numbered.

1-5. In-gel Protein Digestion for Mass Spectrometry Analysis

Protein spots were enzymatically digested into small fragments using modified porcine trypsin according to a method described in Shevchenko et al., Anal. Chem. 1996, 68:850-858).

In brief, differentially expressed protein spots were excised from gels. Gel pieces containing the protein spots were washed in 50% acetonitrile (ACN) to remove impurities including SDS, an organic solvent and a staining reagent. For trypsin digestion, the gel pieces were then rehydrated and digested in a trypsin digestion solution (8-10 ng/µl of trypsin in trypsin digestion buffer (5% ACN, 5% $NH_4HCO_3$, 90% DW); 5 µl/spot) at 37° C. for 8-10 hrs. The trypsin digestion was stopped by addition of 5 µl of 0.5% trifluoroacetic acid. The trypsin-digested peptides were extracted in an aqueous solution. The solution was desalted and concentrated into a volume of 1-5 µl using a C18 ZipTip (Millipore, USA). The concentrate was mixed with the same volume of a matrix solution (α-cyano-4-hydroxycinnamic acid saturated in 50% aqueous acetonitrile), and subjected to mass spectrometry analysis.

1-6. Protein Identification Using Mass Spectrometry

Mass spectra were recorded using an Ettan MALDI-TOF mass spectrometer (Amersham Biosciences). The samples prepared in Example 1-5 were spotted onto a target plate, evaporated through radiation with a pulsed N2 laser of 337 nm, and accelerated with a 20-kV injection pulse. Each mass spectrum for protein spots was the cumulative average of 300 laser shots. Spectra were calibrated using trypsin autodigestion peptide ion peak m/z (842.510, 2211.1046) as internal standards.

The search program ProFound, which was developed by the Rockefeller University, was used for protein identification from the mass spectra.

As a result, a total of nine proteins were identified to be significantly upregulated in renal cell carcinoma. The differentially expressed proteins included nicotinamide N-methyltransferase (NNMT), L-plastin, secretagogin (SCGN), human neuron specific enolase (hNSE), endotherial cell growth factor-1 (ECGF-1), ferritin light subunit, NM23A, actin regulatory protein (CapG), and C4aANA.

Of the identified proteins, NNMT, L-plastin, secretagogin (SCGN), CapG, NM23A and C4aANA were found to be unknown for their increased expression in renal cell carcinoma.

Figure 7:
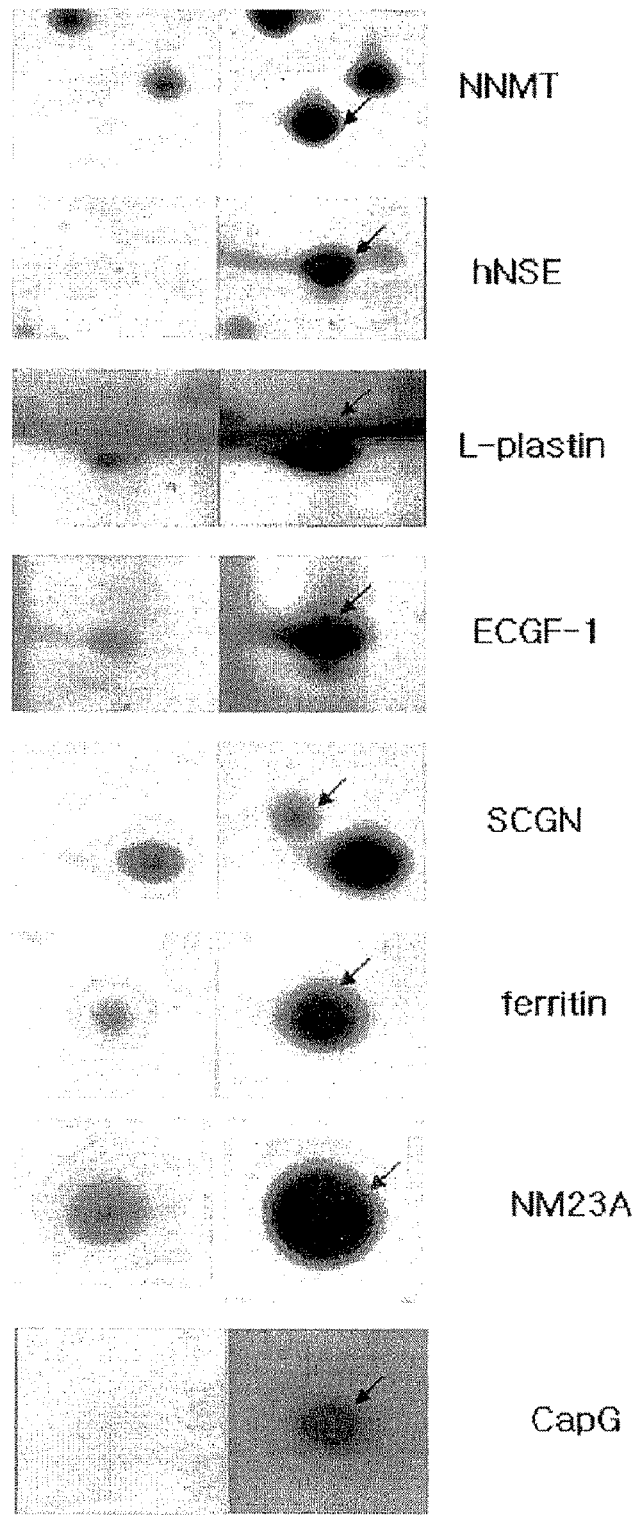
FIG. 7 shows enlarged views of eight protein spots showing a significant increase in expression in cases of renal cell carcinoma in the 2D gel images of FIGS. 1, 2, 5 and 6, the eight proteins including NNMT, hNSE, L-plastin, ECGF-1, SCGN, ferritin light subunit, NM23A and CapG.
Figure 8:
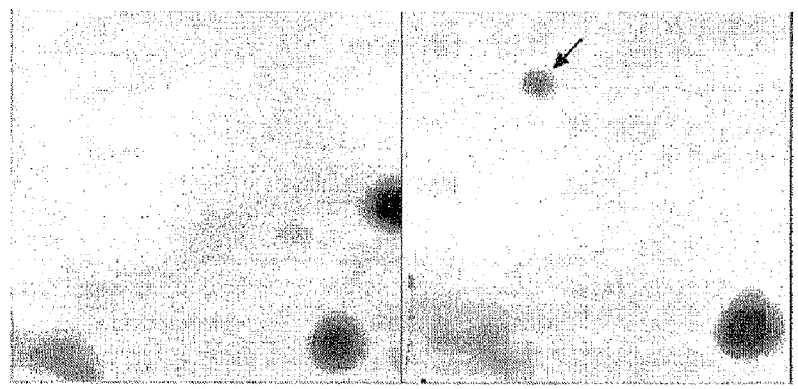
FIG. 8 shows an enlarged view of a spot of a protein showing a significant increase in expression in cases of renal cell carcinoma, namely C4aANA, in the 2D gel image of FIG. 4, wherein the protein spot is compared to the corresponding region in the gel image of FIG. 3.
Figure 9:
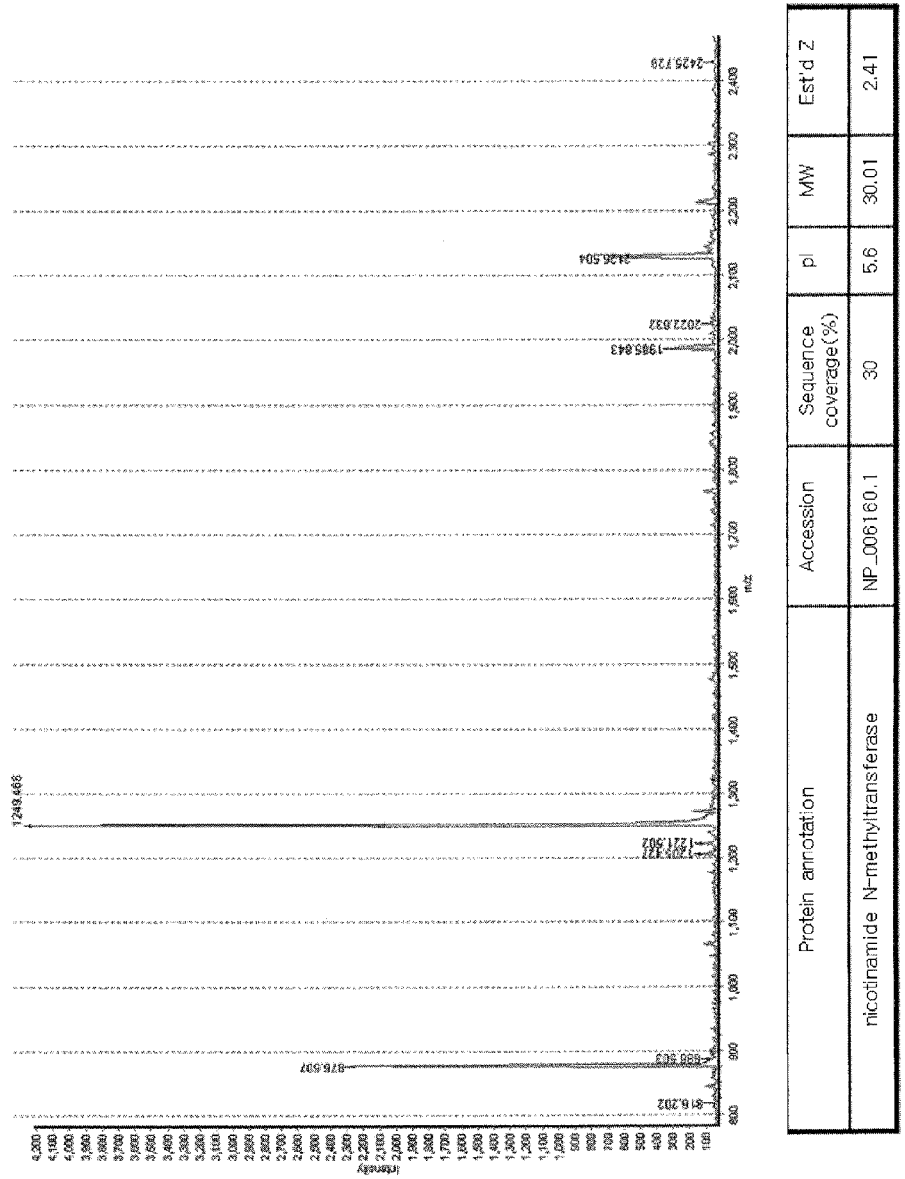
FIGS. 9 to 17 show mass spectra of NNMT, L-plastin, SCGN, hNSE, ECGF-1, ferritin, NM23A, CapG and C4aANA, respectively, and the results of protein identification using the search program ProFound.
Figure 10:
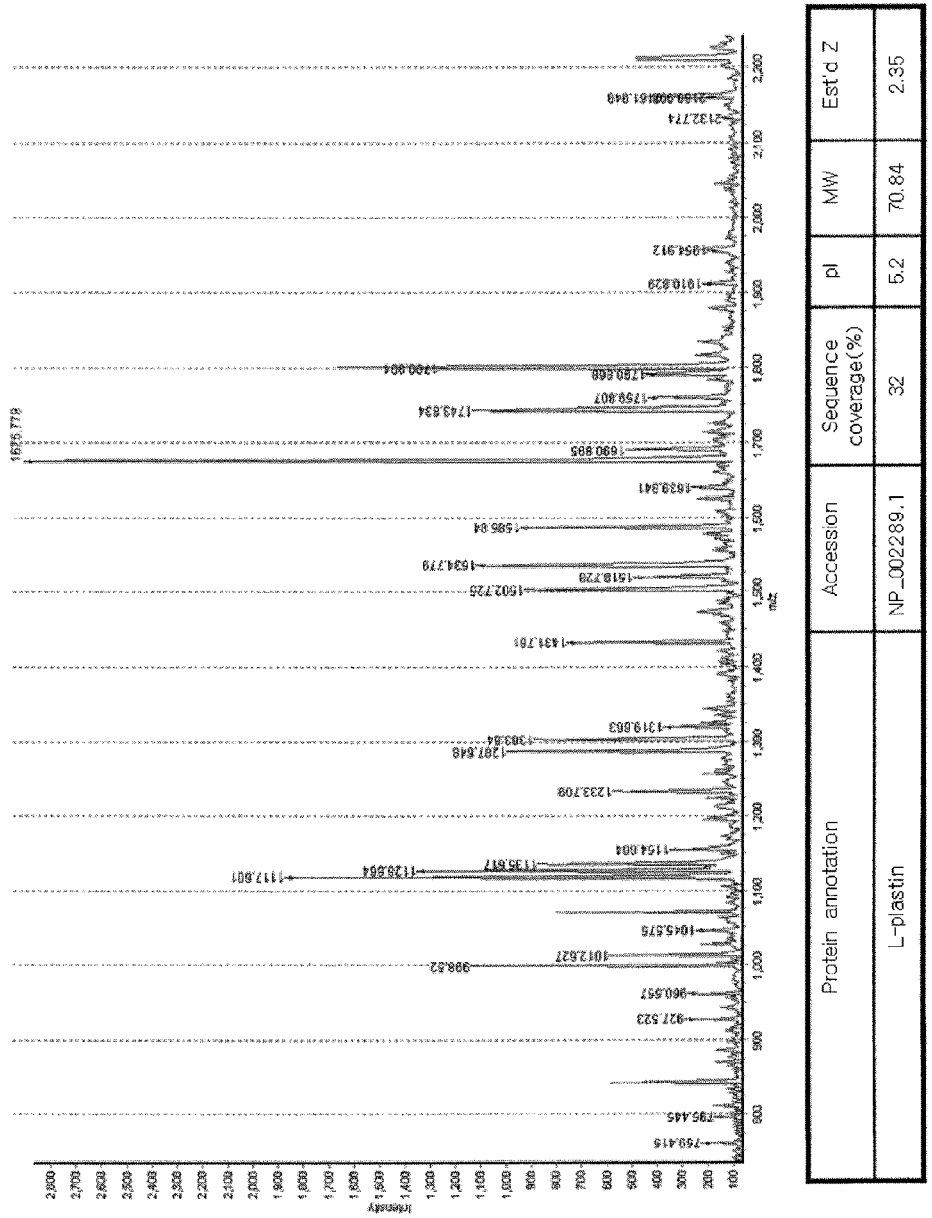
Figure 11:
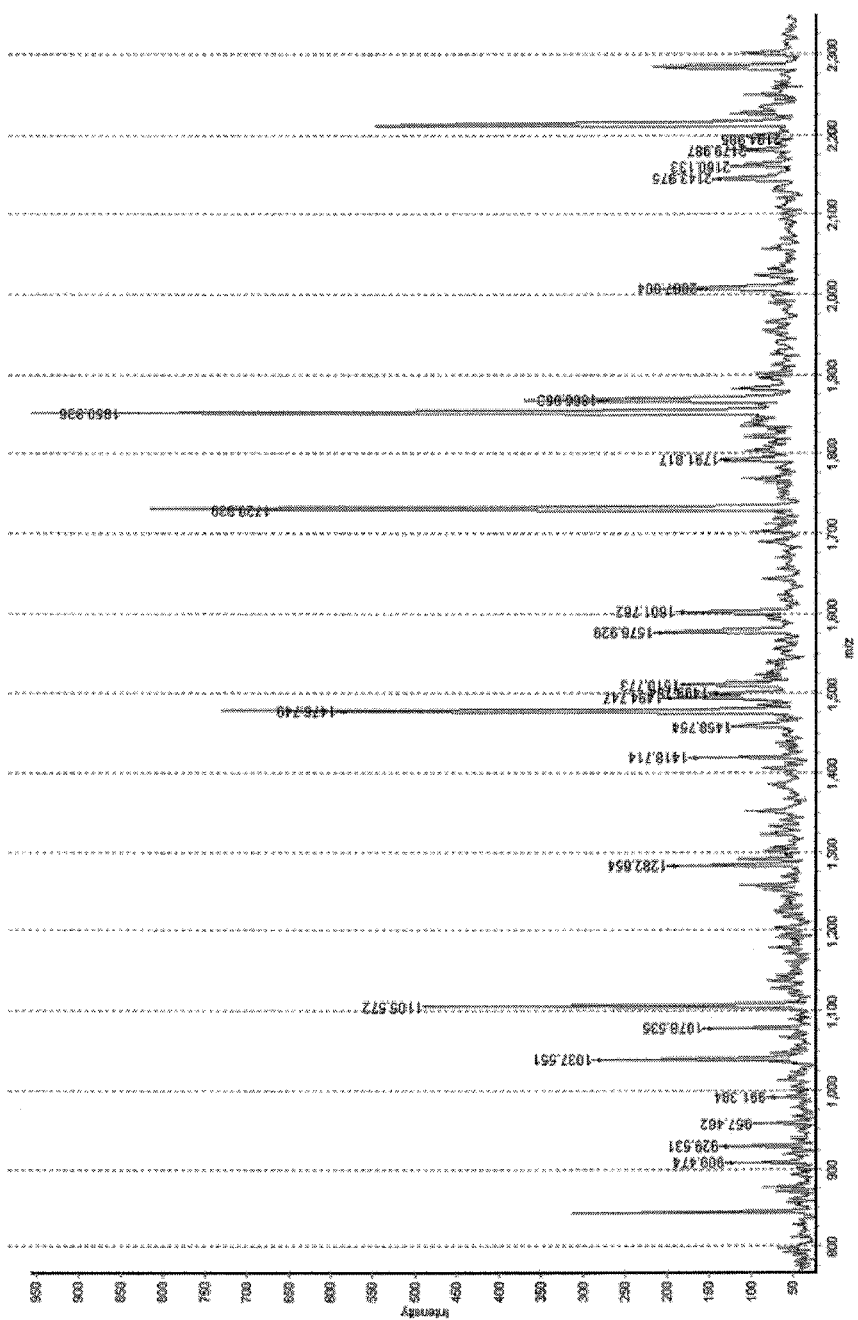
Figure 12:
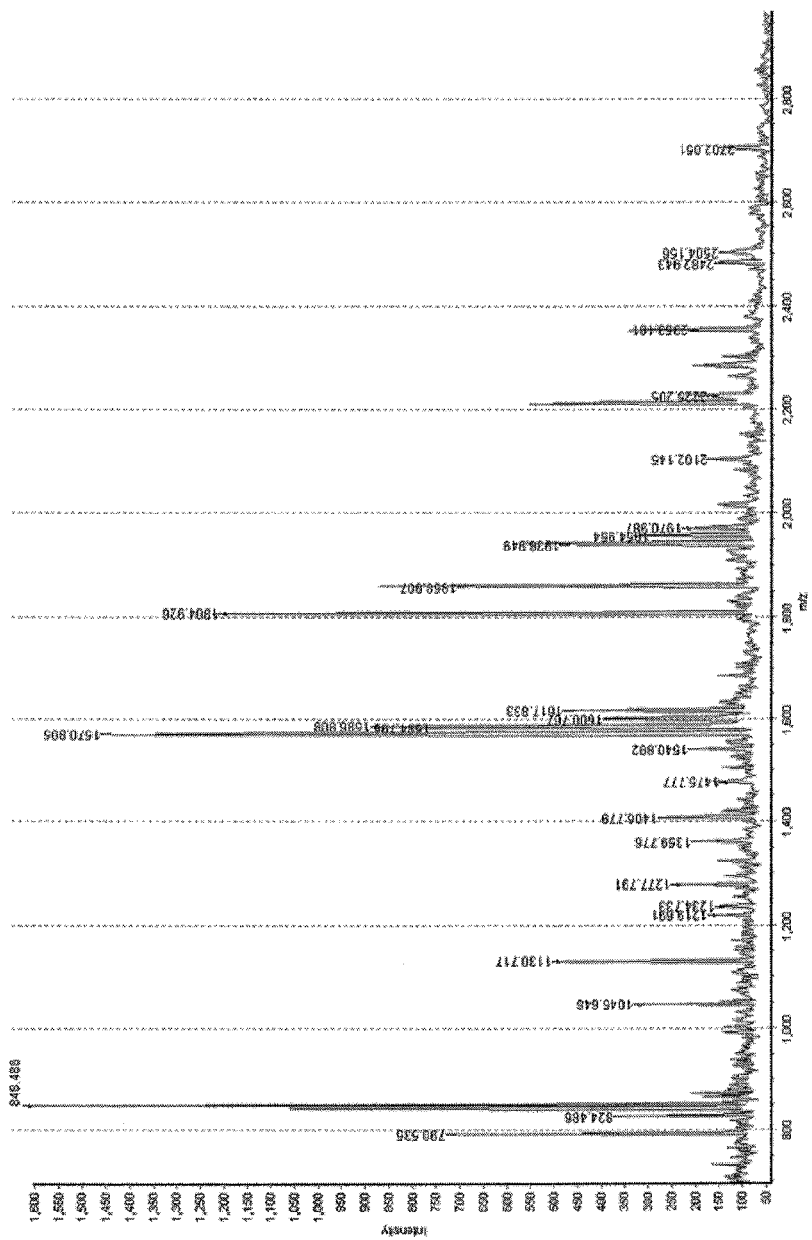
Figure 13:
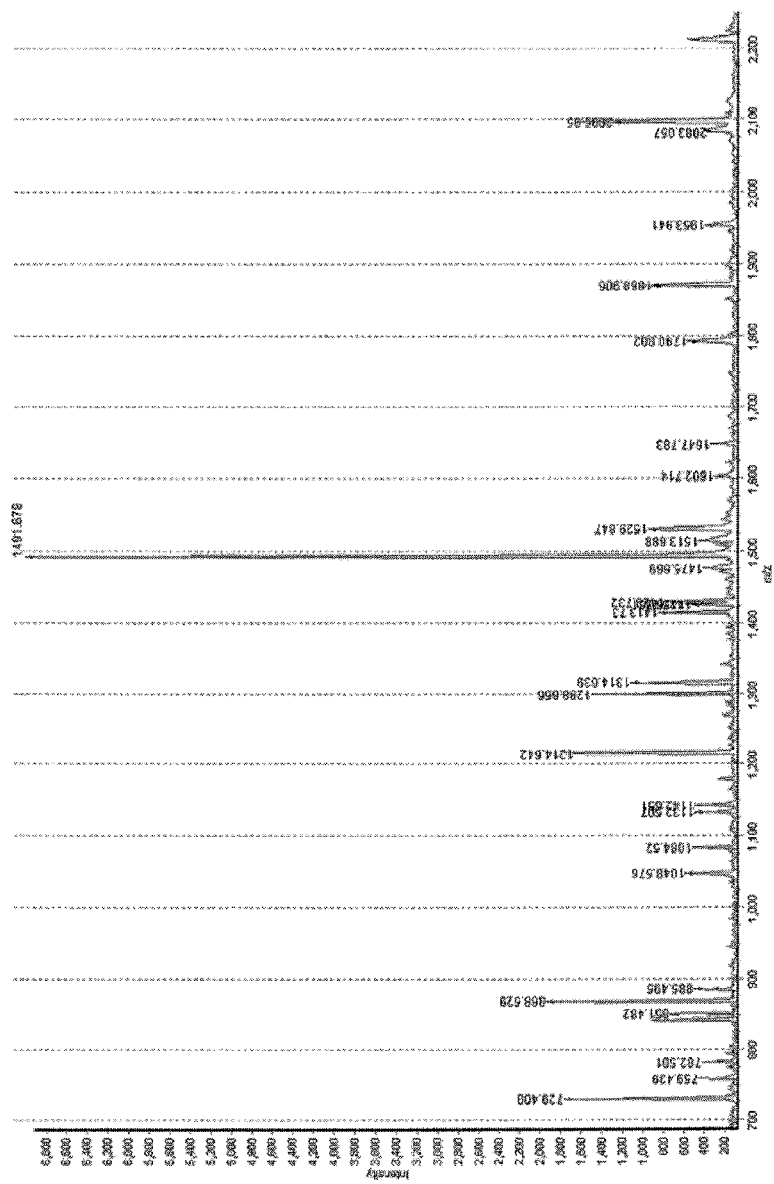
Figure 14:
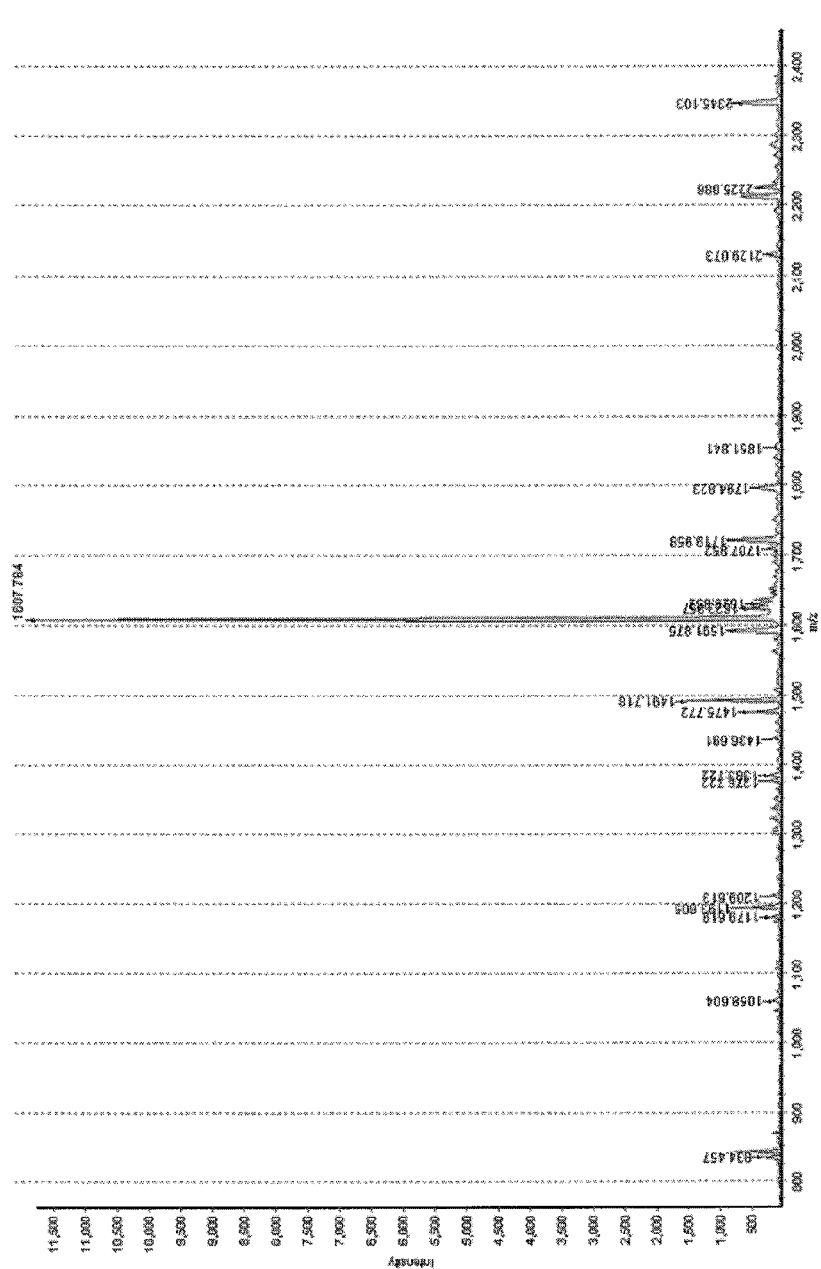
Figure 15:
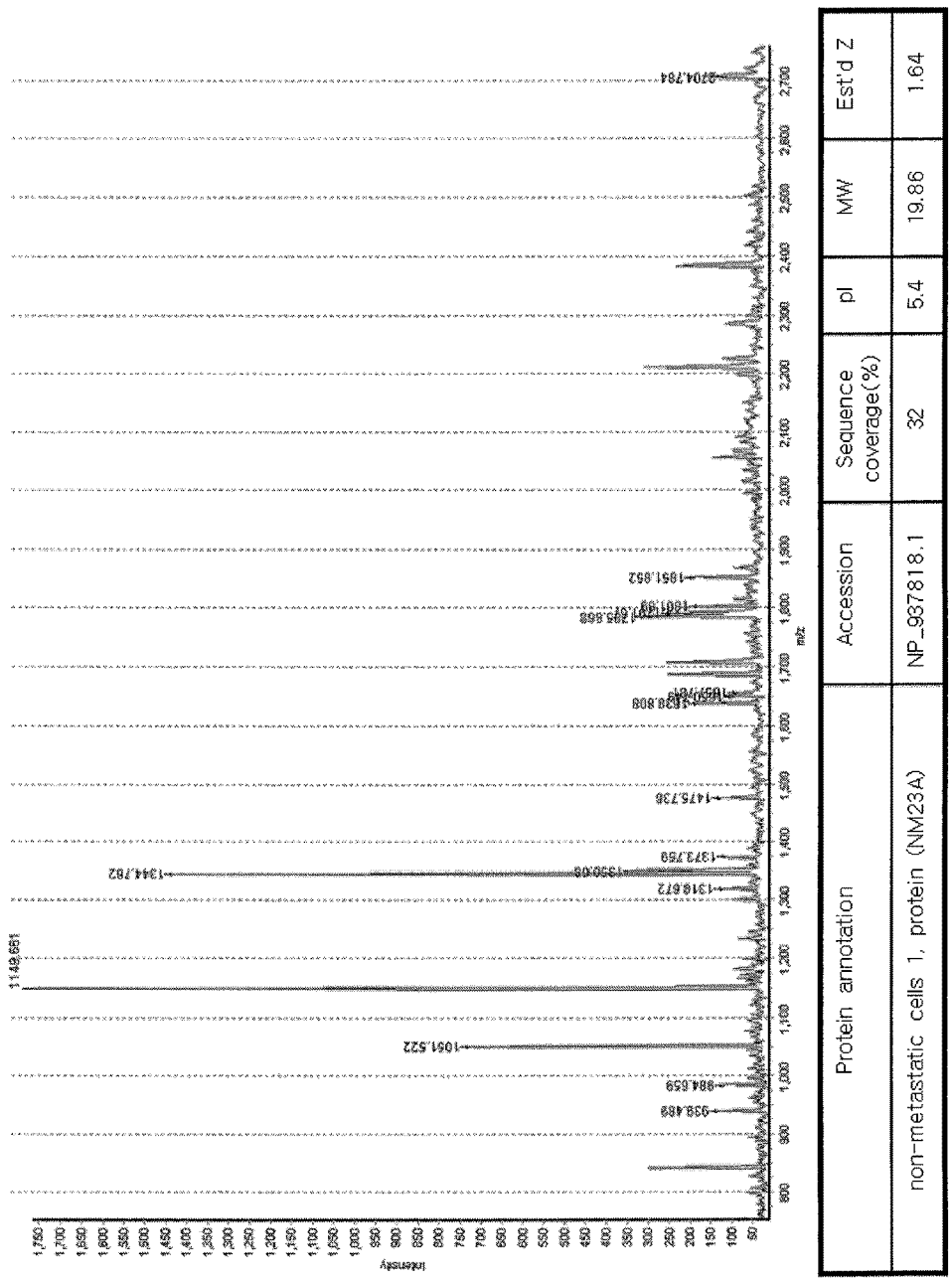
Figure 16:
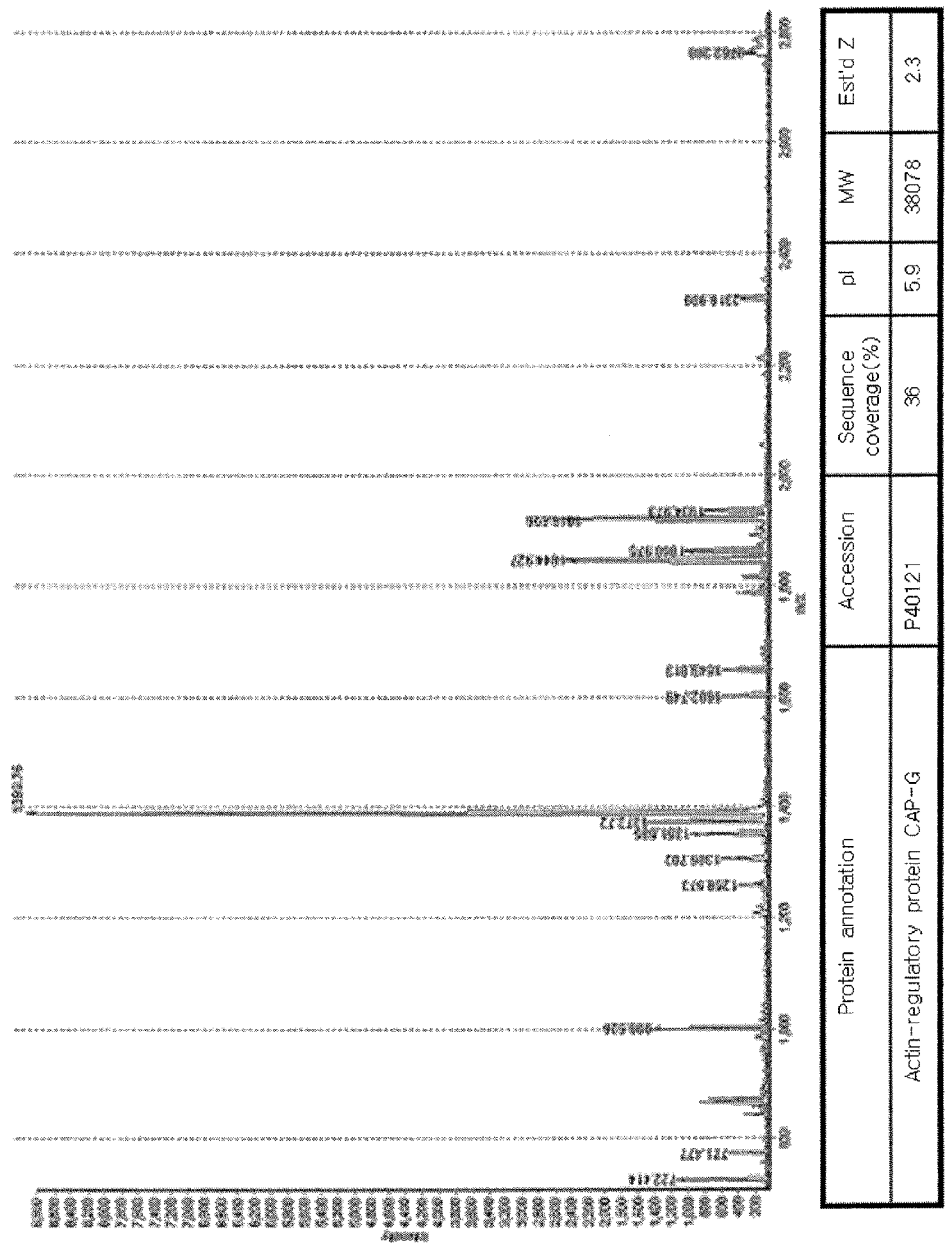
Figure 17:
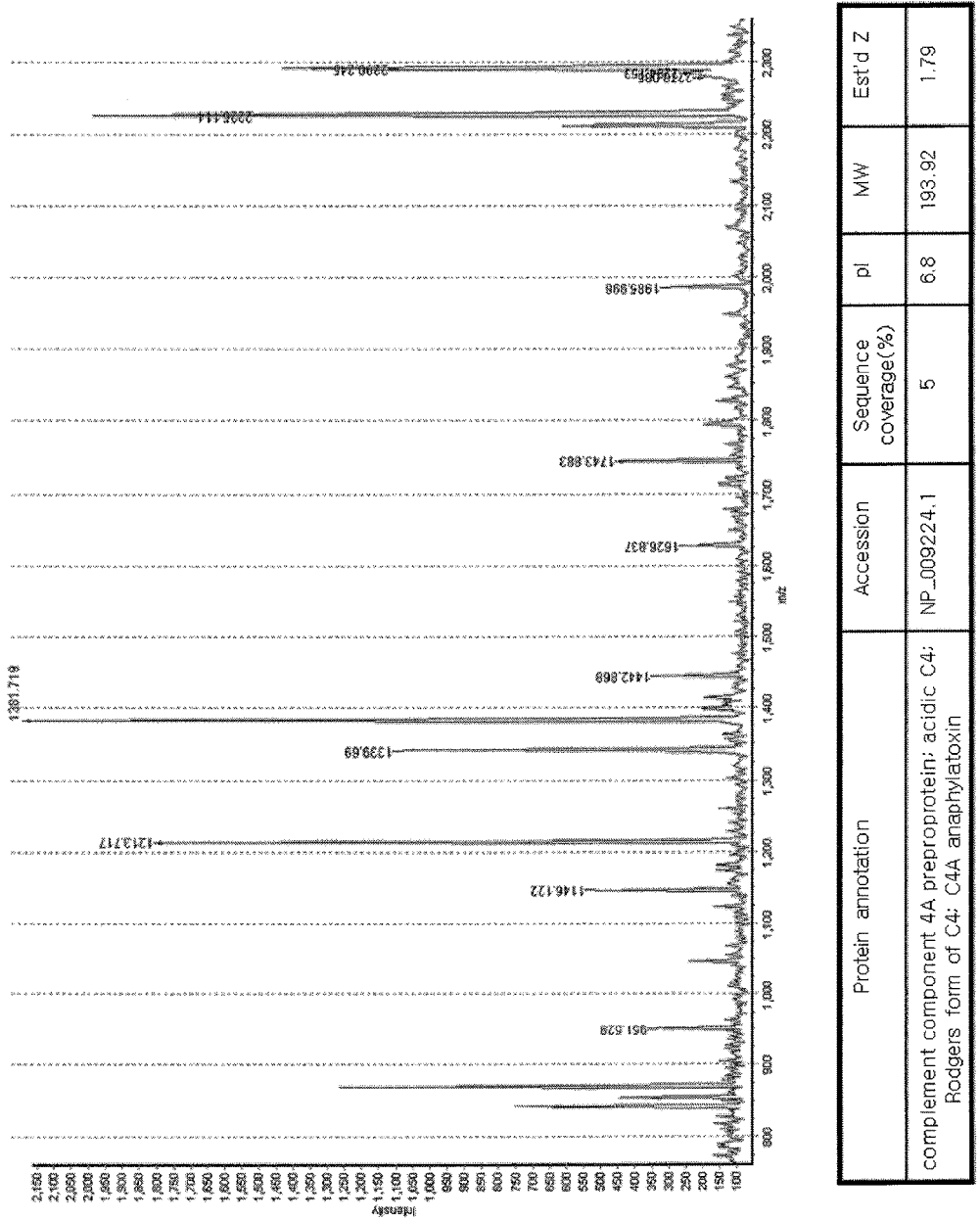

FIG. 7 shows enlarged views of eight protein spots showing a significant expression increase in renal cell carcinoma in the 2D gel images of FIGS. 1, 2, 5 and 6, the eight proteins including NNMT, hNSE, L-plastin, ECGF-1, SCGN, ferritin light subunit, NM23A and CapG. FIG. 8 shows an enlarged view of a spot of a protein showing a significant expression increase in renal cell carcinoma, namely C4aANA, in the 2D gel image of FIG. 4, wherein the protein spot is compared to the corresponding region in the gel image of FIG. 3.

FIGS. 9 to 17 show mass spectra of NNMT, L-plastin, SCGN, hNSE, ECGF-1, ferritin, NM23A, CapG and C4aANA, respectively, and the results of protein identification using the search program ProFound.

The test results were obtained using clear-cell RCC kidney tissues. However, when the inventors of this application tested tissue samples from other types of renal cell carcinoma (papillary RCC and chromophobe RCC) according to the same procedure as described above, the above seven proteins exhibited increased expression in cancerous kidney tissues albeit it a small one, compared to normal kidney tissues.

EXAMPLE 2

Evaluation of Differential Expression of NNMT Between Normal and Cancerous Kidney Tissues Using Western Blotting Among the proteins identified to be upregulated in renal cell carcinoma, NNMT was assessed for its differential expression between normal and cancerous kidney tissues using Western blotting.

2-1. Preparation of a Recombinant NNMT Antigen

In order to clone an NNMT gene into pBAD/Myc-His A, which is a vector of protein large expression, PCR was carried out using a forward primer having a XhoI site (5'-CTC GAG AGA ATC AGG CTT CAC CTC CAA GGA-3') and a reverse primer having a HindIII site (5'-AAG CTT CAG GGG TCT GCT CAG CTT CCT C-3').

The amplified NNMT gene was cloned into a pBAD/Myc-His A vector, and transformed into *E. coli* (BL21) for large expression of NNMT. An *E. coli* clone was identified to carry a recombinant NNMT gene fused to a C-terminal 6 histidine tag of the pBAD/Myc-His A vector. The clone was grown in a Luria-bertani broth medium supplemented with 100 mg/L ampicillin at 37° C. with agitation. When $OD_{600}$ reached 0.5, a 20% arabinose solution was added to the medium at a final concentration of 0.2-0.0002%, and cells were further grown for 3 hrs in order to induce NNMT overexpression. The culture was centrifuged at 8,000 rpm for 15 min. The cell pellet was recovered and stored at −70° C. until protein purification.

2-2. NNMT Purification

The *E. coli* cells, in which the NNMT protein was overexpressed, were suspended in a six volume of a buffer (50 mM Tris-HCl, pH 7.5, 5 mM immidazol), and disrupted through sonication at a duty cycle of 50% four times for 2 min each. The cell lysate was subjected to high-speed centrifugation in order to remove insoluble materials. The supernatant was passed through a Ni-NTA column equilibrated with a buffer (50 mM Tris-HCl, pH 7.5, 5 mM immidazol), and the column was washed with a ten-fold volume of the same buffer. The column was then eluted with 100 mM immidazol. The eluate was dialyzed in a buffer containing 150 mM NaCl.

2-3. Antibody Production and Purification Immunization was performed using the purified NNMT protein in order to prepare an antibody against NNMT. The NNMT protein (0.1 mg/ml) was mixed with a fresh incomplete adjuvant at a 1:1 ratio, and the resulting suspension was injected intraperitoneally into a rabbit. One week after the primary immunization, the immunogen was injected again. Two weeks after the second immunization, a final immunization was carried out through subcutaneous injection of a fresh complete adjuvant. A blood sample was collected the immunized rabbit. The blood was allowed to clot in order to remove blood cells, and the remaining serum, containing antibodies, was recovered.

The antibody molecules were isolated as follows. A protein A column was equilibrated with a buffer (50 mM Tris-HCl, pH 7.0), and the serum sample was diluted in a five volume of the same buffer. The diluted serum was then loaded to the equilibrated column. After the column was washed with a five volume of the same buffer, it was eluted with an elution buffer (Glycin-HCl, pH 3.0). The eluate was neutralized with a neutralization buffer (Tris-HCl, pH 8.8). The eluted antibody was dialyzed in a buffer (50 mM phosphate, pH 7.4), and stored at −20° C. until use.

2-4. Western Blotting for Detecting NNMT Expression

Western blotting was carried out in order to detect the NNMT protein in renal cell carcinoma and to assess the expression level of the protein.

Protein samples (2 mg/ml) from normal and cancerous kidney tissues were diluted in a 4× sample buffer, and 10 µl of each dilute was loaded onto a 12% SDS-PAGE gel. The gel was developed at 110V. The proteins separated on the gel were electrically transferred onto a PVDF membrane. After the blot was blocked in 5% skimmed milk/PBST (0.05% Tween 20), it was primarily incubated in biotinylated anti-NNMT IgG in 5% skim milk/PBST (diluted in 1:10,000) and then probed with streptavidin-HRP (diluted in 1:10,000). The blot was developed using an ECL reagent.

Figure 18:
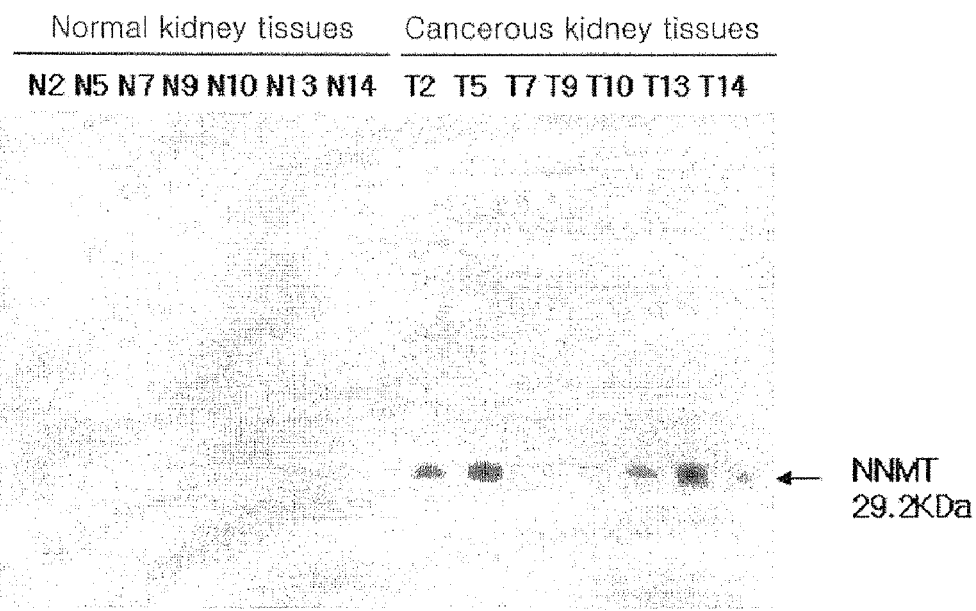
FIG. 18 shows the results of immunoblotting for NNMT expression in normal and cancerous kidney tissues.

The results are shown in FIG. 18.

EXAMPLE 3

Evaluation of the Potential of the Identified Proteins as Diagnostic Markers

The expression levels of NNMT in samples from fourteen renal cell carcinoma patients and fifteen normal individuals were assessed to determine whether the NNMT protein has potential as a diagnostic marker for renal cell carcinoma. The diagnostic accuracy was assessed through receiver operating characteristic (ROC) analysis. ROC analysis of renal cell carcinoma patients showed good results, a sensitivity of 92.3 and a specificity of 93.7. ROC analysis using a combination of NNMT and one or more selected from L-plastin, SCGN, hNSE, ECGF-1 and ferritin showed higher accuracy than the single use of NNMT. These results indicated that the identified proteins are useful as diagnostic markers of renal cell carcinoma.

EXAMPLE 4

Detection of NNMT in Plasma Using ELISA

An anti-NNMT antibody was adjusted to a final concentration of 0.1 mg/ml in 50 mM ammonium bicarbonate (pH 9.6). 10 µl (10 µg) of the antibody was added to each well of a plate, and the plate was incubated at 4° C. overnight to immobilize the antibody. The plate was washed with 150 µl of a washing buffer (PBST, 10 mM sodium phosphate, pH 7.4, 0.9% NaCl, 0.05% Tween 20) three times, and incubated in 200 μl of a blocking buffer (0.1% casein, 20 mM sodium phosphate, pH 7.4, 0.9% NaCl) to block the space between antibody molecules. 10 μl of each serum sample from patients and normal individuals was diluted in 90 μl of a reaction buffer (PEST, 0.1% casein), added to each well, and incubated for 2 hrs to allow antigen-antibody complex formation. Then, the plate was washed with 150 μl of the washing buffer three times, incubated for 1 hr in 100 μl of a biotin-conjugated antibody (biotin-rabbit anti-h6-NNMT IgG (1 mg/ml), diluted in 1:2,000 in the reaction buffer), and then washed with 150 μl of the washing buffer three times. For development, 100 μl of a 1:10,000 dilution of Stratavidin-HRP (1 mg/ml) was added to each well, and the reaction was allowed to occur for 1 hr. After the plate was washed with 150 μl of the washing buffer five times, 100 μl of a TMB solution (Sigma, USA) was added to each well and incubated for 8-10 min. The color reaction was stopped by adding 50 μl of 0.5 N sulfuric acid to each well. Absorbance was measured at 450 nm using an ELISA Reader (Molecular Dynamics, USA).

EXAMPLE 5

Evaluation of Clinical Usefulness of NNMT Using ROC Analysis

The accuracy of a diagnostic method based on the differential expression of NNMT was assessed through ROC analysis using plasma samples from 40 normal individuals and plasma samples from a total of 41 patients afflicted with conventional RCC, papillary RCC and chromophobe RCC. ROC analysis was performed using a MedCale program. As a result, the diagnostic method was found to have an AUC of 0.80 and thus to have high accuracy in discriminating between normal individuals and RCC patients.

[Sequence List]
Attached.

We claim:

1. A method for diagnosing renal cell carcinoma in a patient comprising steps of:
   preparing a composition containing a binding molecule that specifically binds NNMT protein;
   contacting the composition with a biological sample from a patient to measure expression level of NNMT protein, wherein the biological sample is a sample selected from the group consisting of a blood sample, a serum sample and a plasma sample; and
   comparing the expression level of NNMT protein in the biological sample from the patient with the expression level of NNMT protein in a corresponding biological sample from a normal individual; and
   classifying a patient with an elevated expression level of NNMT protein as having renal cell carcinoma.

2. The method according to claim 1, wherein the binding molecule is an antibody and the antibody is one or more selected from the group consisting of a monoclonal antibody, a polyclonal antibody, a multispecific antibody, a fragment of the antibody, a recombinant antibody, and a chemically modified antibody.

3. The method according to claim 2, wherein the antibody fragment is Fab, F(ab')$_2$, scFv, Fv, Fab/c, a digestion product of an antibody using a proteolytic enzyme, or an antibody prepared using a recombinant DNA technique.

4. The method according to claim 2, wherein the antibody is a monoclonal antibody or a polyclonal antibody.

5. The method according to claim 4, wherein the monoclonal antibody is prepared using a method of producing a monoclonal antibody comprising immunizing a mammal with the renal cell carcinoma marker and collecting antibody-producing cells, fusing the antibody-producing cells with myeloma cells to establish a hybridoma, and obtaining the monoclonal antibody from the hybridoma.

6. The method according to claim 5, wherein the antibody-producing cells are splenocytes (spleen cells), lymph node cells, or peripheral blood cells.

7. The method according to claim 5, wherein the mammal is a rat, a mouse, a rabbit, or a monkey.

8. The method according to claim 5, wherein the myeloma cells are derived from an animal of the same species as the mammal, have drug selectivity, and cannot survive in an HAT selection medium supplemented with hypoxanthine, aminopterin and thymidine in a state of being not fused with splenocytes, but can survive in a state of being fused with splenocytes.

9. The method according to claim 5, wherein the renal cell carcinoma marker is a fragment of a full-length protein.

* * * * *